United States Patent [19]

Ciganek

[11] 4,088,772
[45] May 9, 1978

[54] METHANODIBENZOCYCLOHEPTAPYRROLES

[75] Inventor: Engelbert Ciganek, Kennett Square, Pa.

[73] Assignee: E. I. Du Pont de Nemours and Company, Wilmington, Del.

[21] Appl. No.: 663,430

[22] Filed: Mar. 3, 1976

Related U.S. Application Data

[63] Continuation-in-part of Ser. No. 545,001, Jan. 30, 1975, abandoned, which is a continuation-in-part of Ser. No. 448,686, Mar. 6, 1974, abandoned.

[30] Foreign Application Priority Data

Feb. 11, 1975 Sweden .............................. 7501519

[51] Int. Cl.$^2$ .................. C07D 209/44; A61K 31/40

[52] U.S. Cl. ................. 424/274; 260/325 R; 260/326.1; 260/332.2 R; 260/347.2; 260/347.3; 260/347.4; 260/558 R; 260/558 A; 260/558 P; 260/559 R; 260/559 A

[58] Field of Search ...................... 260/326.1; 424/274

[56] References Cited

U.S. PATENT DOCUMENTS

| | | | |
|---|---|---|---|
| 3,687,936 | 8/1972 | Wilhelm | 260/239 B |
| 3,726,897 | 4/1973 | Schindler et al. | 260/313.1 |

FOREIGN PATENT DOCUMENTS 1,336,634  11/1973  United Kingdom ............. 260/268 P

*Primary Examiner*—Raymond V. Rush
*Attorney, Agent, or Firm*—Anthony P. Mentis

[57] ABSTRACT

Methanodibenzocycloheptapyrroles, such as 2-cyclopentylmethyl-2,3,8,12b-tetrahydro-1H-3a, 8-methanodibenzo[3,4:6,7]cyclohepta[1,2-c]pyrrole, useful as tranquilizers and analgesics.

43 Claims, No Drawings

METHANODIBENZOCYCLOHEPTAPYRROLES

RELATED APPLICATIONS

This application is a continuation-in-part of applicant's copending application Ser. No. 545,001 filed 30 Jan. 1975, now abandoned which is a continuation-in-part of application Ser. No. 448,686, filed 6 Mar. 1974, now abandoned.

BACKGROUND

This invention relates to nitrogen containing polycyclic tranquilizers.

Ciba-Geigy, in British Pat. No. 1,336,634, discloses 5,10-methanodibenzo[a,d]cycloheptene derivatives with the following basic structure;

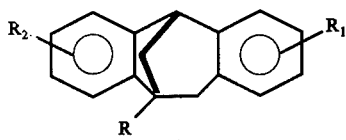

Wilhelm, in U.S. Pat. No. 3,687,936, discloses 11-aminoaliphatic-5,10-methanodibenzo[a,d][1,4]cycloheptadienes with the following basic structure:

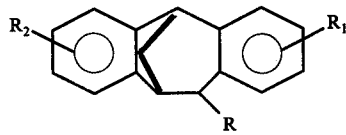

Schindler, et al., in U.S. Pat. No. 3,726,897, disclose 1,2,3,8-tetrahydrodibenzo(3,4:6,7)cyclohepta[1,2-c]pyrroles with the following basic structure:

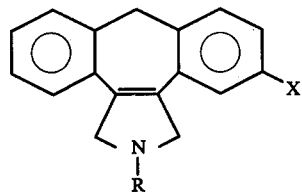

With the ever increasing knowledge about the biological basis of mental illness and the development of the discipline of "biological psychiatry", there is a continuing need for psychotherapeutic agents with fewer side effects and new modes of action.

The present invention results from efforts to develop new, safe, and effective psychotherapeutic agents with minimal side effects.

SUMMARY

According to this invention there is provided compounds of the formula

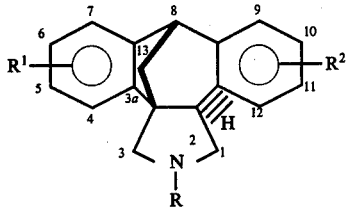

where
$R^1$ and $R^2$, the same or different = hydrogen, lower alkyl, lower alkoxy, hydroxyl, fluorine, chlorine, bromine, 2,2,2-trifluoroethyl, carboxyl, methoxycarbonyl, ethoxycarbonyl, N-methylsulfamyl, lower alkylcarbonyl, cycloalkylcarbonyl of 4–7 carbons, nitro, amino, acetamido, formyl, cyano, azido, fluoromethyl, difluoromethyl, formyloxime, acetyloxime, $$-CH=NO\overset{O}{\overset{\|}{C}}-NHCH_3, \text{ and } -\overset{OH}{\overset{|}{CH}}-R^6 \text{ where } R^6 \text{ is hydrogen,}$$

lower alkyl, or alkenyl of 3–4 carbons; provided, that only one of $R^1$ and $R^2$ is nitro;

R = hydrogen, alkyl of 1–10 carbons, alkenyl of 3–7 carbons attached by a saturated carbon to N, cycloalkyl of 3–5 carbons, propargyl, α-furylmethyl, α-tetrahydrofurylmethyl, α-thienylmethyl; and —$(CH_2)_nCN$, —$(CH_2)_nCOOH$, —$(CH_2)_qOR^3$, —$(CH_2)_nCOO$ (lower alkyl), and —$CH(R^4)(CH_2)_pR^5$ of up to 14 carbons, where
$n$ = 1–6;
$p$ = 0–5;
$q$ = 2–6;
$R^3$ = lower alkyl, phenyl, or lower alkylphenyl;
$R^4$ = hydrogen or n-lower alkyl;
$R^5$ = a hydrocarbyl group containing at least one ring of 3–9 carbons attached to alkylene by a ring carbon; provided, when $p$ = 0, the carbon attached to —$CH(R^4)$- is not a quaternary carbon; and tertiary amine oxide when R is other than hydrogen.

Also included are pharmaceutical compositions containing compounds where R is other than hydrogen, and methods of using these compounds as tranquilizers and analgesics in mammals.

Compounds where R is hydrogen are intermediates for making the pharmacologically active compounds.

DETAILED DESCRIPTION

For the purpose of this disclosure the following term will have these meanings:

"lower alkyl": an alkyl group of one to four carbon atoms, including branched alkyl groups.

"cycloalkyl group": a radical derived from a ring of —$CH_2$— groups by removal of a hydrogen atom.

"quaternary carbon atom": a carbon atom joined directly to four other carbon atoms.

"cycloalkenyl": cyclic hydrocarbon group containing one or more double bonds formally derived from a cycloalkyl group by removal of hydrogen.

Preferred Compounds

Preferred for their higher activity are those compounds where $R^1$ and $R^2$ are hydrogen.

Most preferred are those compounds where:
$R^1$ and $R^2$ are hydrogen; and R is alkyl of 1–10 carbons, especially n-alkyl of 2–8 carbons; alkenyl of 3–7 carbons attached to N by a saturated carbon atom, especially allyl;
α-furylmethyl;
—$(CH_2)_q$-O-lower alkyl;
—$(CH_2)_q$-O-phenyl; and
—$CH(R^4)(CH_2)_p R^5$
where
$p = 0-3$;
$q = 2-6$;
$R^4 = H$ or $CH_3$;
$R^5$ = cycloalkyl of 3–8 carbons; cycloalkenyl of 3–8 carbons, methylenecycloalkyl of 4–9 carbons; polycycloalkyl of 7–9 carbons; polycycloalkenyl of 7–9 carbons; or phenyl.

Most preferred are those compounds where $R^1$ and $R^2$ are hydrogen; and R is cycloalkylmethyl of 5–10 carbons or alkyl of 3–8 carbons.

The two most preferred compounds are:
2-cyclopentylmethyl-2,3,8,12b-tetrahydro-1H-3a,8-methanodibenzo[3,4:6,7]cyclohepta[1,2-c]pyrrole
2-cyclohexylmethyl-2,3,8,12b-tetrahydro-1H-3a,8-methanodibenzo[3,4:6,7]cyclohepta[1,2-c]pyrrole Synthesis These compounds can be made by a rearrangement reaction of bridged ethenoanthracenes, which are made by an internal Diels-Alder reaction of propargyl-substituted 9-anthracenemethylenimines, 9-anthracenemethylamines and 9-anthramides.

In one procedure a substituted anthracene of the formula:

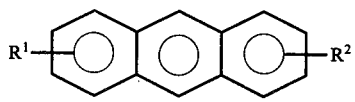

where $R^1$ and $R^2$ can be hydrogen, lower alkyl, lower alkoxy, fluorine, chlorine, bromine, nitro, 2,2,2-trifluoroethyl or other partially fluorinated lower alkyl groups, cyano, carboxyl, alkoxycarbonyl, N-methylsulfamyl, or alkylcarbonyl groups, is reacted with oxalyl chloride in the presence of a catalyst to obtain the corresponding 9-anthroyl chloride. The substituted 9-anthroyl chloride is reacted with unsubstituted propargylamine or propargylamine substituted on the nitrogen atom with one of the above R groups. These compounds undergo an internal Diels-Alder reaction to give substituted, 9,12-bridged ethenoanthracenes according to the following equation.

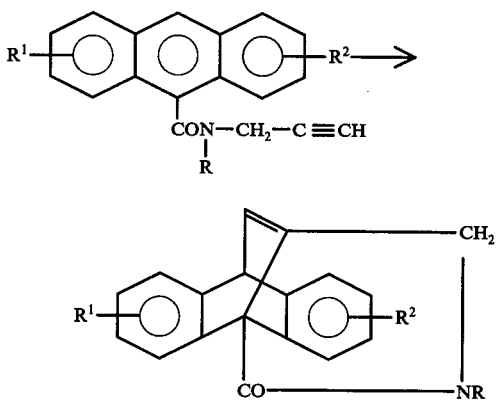

This process can be carried out by heating the alkynylanthramide, either neat or in a suitable inert solvent, preferably an aromatic hydrocarbon, at a temperature of 80° C to 250° C for a time sufficient to effect cyclization, generally from 1 to 48 hours, depending on the conditions.

Reaction of II with bromine lads to a ring rearrangement reaction to produce products with the skeletal stucture of I, (stereochemistry unknown) substituted with bromine at the 12b and 13 positions, and containing a 1-carbonyl group. Bromination can be carried out in any inert solvent. But a chlorinated aliphatic hydrocarbon is preferred and methylene chloride and chloroform are especially preferred. The reaction temperature should be about —20° C – 100° C, preferably 20–35° C. The bromine atoms are readily removed from the intermediate by reductive dehalogenation with a trialkyltin hydride, either neat, or dissolved in an aromatic hydrocarbon solvent. It is preferred to use tributyltin hydride in benzene or toluene. The reaction is carried out at a temperature in the range of 50–180° C to give compounds having the trans skeletal structure of I with a 1-carbonyl group. Alternatively, the bromine atoms can be removed by reaction with zinc and acetic acid at 25° – 120° C, or with zinc and aqueous dimethylformamide.

The amides containing the 1-carbonyl group are readily converted to the corresponding amines of structure I by reduction of the carbonyl group, preferably with diborane dissolved in an ether solvent such as tetrahydrofuran, at a temperature of 0°–100° C.

Another procedure starts with an ethenoanthracene of the formula:

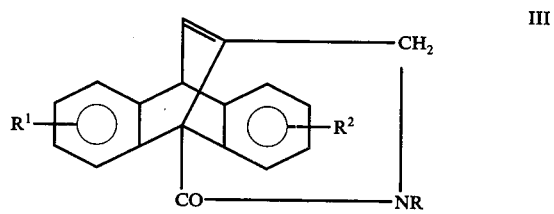

which can be prepared from the corresponding 9-anthraldehyde by reaction with propargylamine. This is followed by internal Diels-Alder reaction, reduction of the carbon-nitrogen double bond, and alkylation of II(R=H) to obtain the N-substituted compound. Alternatively, III(R=H) can be acylated by conventional procedures, and the acyl derivatives can then be reduced with lithium aluminum hydride to obtain the corresponding N-substituted compounds.

In a preferred process for the preparation of III, which is shown in the following equations, the 9-anthraldehyde compound is reacted with a suitable amine at 25° – 150° C in an alcoholic solvent to form an imine. The imine is then reduced with a metal hydride reducing agent, such as sodium borohydride or sodium cyanoborohydride, in an alcohol, such as methanol, ethanol, or isopropanol, which can be the same solvent that is employed to form the imine, at a temperature between 0° C and 100° C. The resultant secondary amine is then condensed with a propargyl halide, preferably propargyl bromide, in the presence of an inorganic base, such as an aqueous solution of an alkali metal carbonate or an organic base that does not react substantially with propargyl bromide, e.g., certain hindered amines, including diisopropylethylamine, at a temperature of 0° – 100° C, preferably ambient temperatures.

The alkynyl-substituted anthracenes are then cyclized to formula III using the method previously described for the cyclization of the alkynylanthramides.

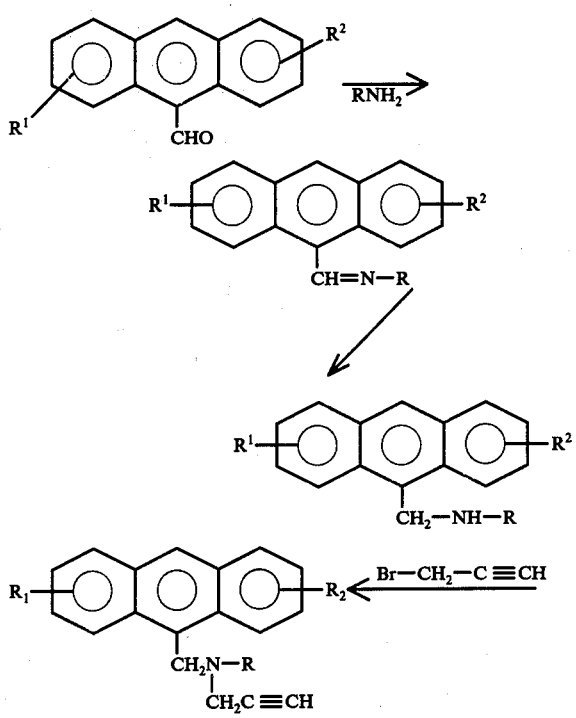

Ring rearrangement of these (III) bridged ethenoanthracenes occurs in the presence of strong acids such as p-toluenesulfonic acid and trifluoroacetic acid at about 70° - 200° C to give products having the skeletal structure of formula I but containing a double bond in the 1–12b position. The rearrangement is preferably carried out with trifluoroacetic acid. This reagent can also be used for the rearrangement of compounds of formula III where R is an acyl group.

The double bond can be reduced to produce the desired trans structure at the 3a–12b carbon atoms by reagents such as sodium cyanoborohydride in acetic acid, or by catalytic hydrogenation with a palladium catalyst in acetic acid solvent, or a platinum or rhodium catalyst in tetrahydrofuran. Reduction with a palladium catalyst in tetrahydrofuran gives a mixture of cis and trans racemates. The carbonyl group of the ring rearrangement product of compounds of formula III where R=acyl must be reduced (e.g., with lithium aluminum hydride) before reduction of the 1–12b double bond, to obtain the desired 3a–12b trans products. Strong bases, e.g., potassium t-butoxide in dimethylsulfoxide, at elevated temperatures, convert predominantly cis racemates to equilibrium mixtures containing predominantly trans racemates. All of these reductions are conveniently run at ambient temperatures, but temperatures between 0° C and 60° C are suitable. When catalytic hydrogenation is used, the pressure of hydrogen should be about 1 - 10 atmospheres.

In this method R must be other than H, and $R^1$ and $R^2$ can be hydrolytically stable groups, including carboxyl groups, which can be subsequently esterified and converted to alkoxycarbonyl or other derived substituents. Hydroxyl-substituted compounds are obtained by cleavage of the corresponding alkoxy compounds.

Compounds of formula I with amino substituents are obtained by reduction of the corresponding nitro compounds. Acetylation of the amino compounds produces the corresponding acetamido derivatives, and diazothization of the amino compounds followed by reaction with azide ion gives the azido derivatives. Conventional aromatic substitution reactions of I ($R^1$, $R^2$ = H) can be employed for preparation of nitro, formyl, alkylcarbonyl, and cycloalkylcarbonyl derivatives. Oximation of the carbonyl-substituted compounds gives the corresponding oximes; and reduction gives the corresponding —CH(OH)$R^6$ compounds. Additionally, halo and hydroxyl derivatives can be obtained by diazotization of the amino compounds followed by reaction with an appropriate conventional reagent. The formyl compounds can also serve as intermediates to carboxyl and methyl compounds by oxidation and reduction respectively. Reaction of a formyl compound with a suitable Grignard reagent also gives —CH(OH)$R^6$ substituted compounds.

Examples of suitable anthracenes that can be used as starting materials include:
1-methylanthracene
2-methylanthracene
2,6-dimethylanthracene
2,7-dimethylanthracene
2-isopropylanthracene
2-t-butylanthracene
1,8-dimethylanthracene
1-chloroanthracene
2-chloroanthracene
1,5-dichloroanthracene
1,8-dichloroanthracene
2-methoxyanthracene
1,5-dimethoxyanthracene
1-bromoanthracene
2-bromoanthracene
3,6-dichloroanthracene
1-fluoroanthracene
2-fluoroanthracene
2,6-dimethoxyanthracene
2-acetylanthracene
1-propionylanthracene
1,5-diacetylanthracene
1,8-diacetylanthracene
1-anthroic acid
2-anthroic acid
1-anthracenesulfonic acid
2-anthracenesulfonic acid
1,8-anthracenedisulfonic acid
2,6-anthracenedisulfonic acid Compounds of formula I where R is H can be alkylated or acylated according to conventional procedures. The acyl derivatives can then be reduced with lithium aluminum hydride to obtain the corresponding N-substituted compounds; for example, cycloalkylmethyl groups can be introduced onto the nitrogen atom by acylation with a cycloalkanecarbonyl chloride followed by reduction of the carbonyl group. The α-furylmethyl and α-thienylmethyl derivatives are obtained in a similar manner.

Alkylation of the R = H compounds is preferred for the introduction of propargyl, ω-cyano lower alkyl, ω-carbomethoxy lower alkyl, ω-carboethoxy lower alkyl, and allyl substituents.

Stereochemistry

In general, the 8, 3a and 12b carbon atoms are asymmetric carbon atoms. Depending on the method of synthesizing the compounds of this invention mixtures of racemates, pure racemates, or optical antipodes are obtained.

The pharmacologically active compounds of this invention are trans at the 3a–12b ring fusion with respect to the 12b-hydrogen atom and the 13-methano bridge as depicted in formula I. The stereochemistry of the 3a–12b ring fusion was determined from the crystal structure of the methiodide salt of the compound of formula I where R = CH₃, and R¹ = R² = H. Crystals of this compound are monoclinic, space group P2₁/c, with cell dimensions of $a = 10.219 \pm 0.008$, $b = 14.759 \pm 0.026$, $c = 12.902 \pm 0.012$A, and $\beta = 100.64 \pm 0.06°$. The C(1)C(12b)C(3a)C(13) torsion angle is -80.6 ± 1.0° and the HC (12b)C(3a)C(13) torsion angle is 162.2 ± 5.0° where H is the hydrogen on C(12b). The C(1)C(12b)C(3a)C(13) torsion angle is the angle between the C(12b)-C(1) and C(3a)-C(13) bonds in the C(12b)-C-(3a) projection (clockwise positive). These data establish that the 3a–12b ring fusion is trans with respect to the 12b-hydrogen atom and the 13-methano bridge.

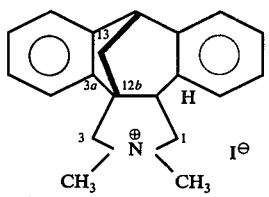

Mixtures of racemates can be separated into the stereoisomeric pure racemates (diasterioisomers) by using known physical procedures, e.g., chromatography or fractional distillation. Pure racemates can be separated into the optical antipodes by conventional methods, such as combination with an optically active acid followed by separation by physical means such as recrystallization of the resultant salts.

In accordance with usual chemical practice the structure of formula I is meant to depict the dl-racemic mixture as well as the d- and l- optical antipodes, which are trans at the 3a–12b ring fusion with respect to the 12b-hydrogen atom and the 13-methano bridge.

The stereoisomer that is the mirror-image of the structure in formula I would be technically illustrated as follows:

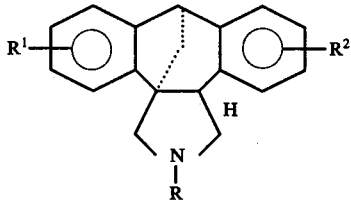

But in following normal chemical practice the structure of formula I is used throughout the specification.

Pharmaceutical Salts

The amine compounds of the present invention can be converted to the amine oxides by oxidation of the parent amine with hydrogen peroxide, peracetic acid, perbenzoic acid, or the like, at ambient temperature, or between about 20° C and 60° C.

The amines or amine oxides can be used as such. For the amines, however, addition salts of the active compound with physiologically acceptable acids known in the art can be used for administration to mammals. Pharmaceutically suitable acid addition salts of these compounds include hydrochloride, sulfate, phosphate, nitrate, citrate, maleate, acetate, tartrate, lactate, fumarate, and the like. The salts can be made and the free bases recovered by conventional methods, including the use of ion exchange resins, metathetical reactions, and the like.

The pharmaceutically suitable salt most preferred is the hydrochloride.

The preparation of these compounds is further illustrated by the following examples. Parts are by weight and degrees centigrade unless otherwise specified.

EXAMPLE 1

2-Methyl-2,3,8,12b-tetrahydro-1H-3a,8-methanodibenzo[3,4:6,7]cyclohepta[1,2-c]pyrrole

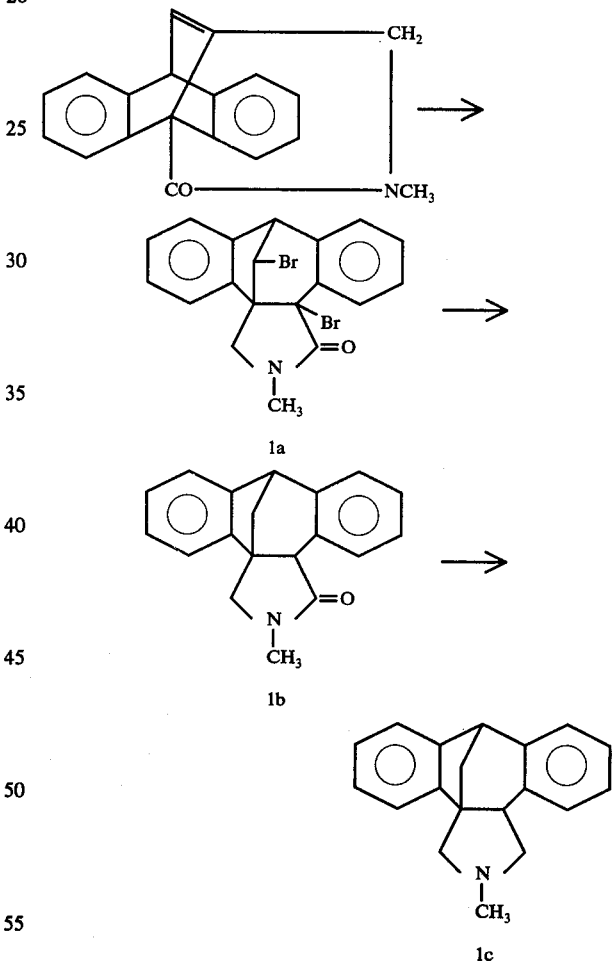

To a solution of 0.88 g of 2-methyl-3,5-dihydro-5,9-b-o-benzenobenz[e]isoindol-1-(2H)-one in 10 mol of methylene chloride is added 0.58 g of bromine in 10 ml of methylene chloride. Removal of the solvent leaves 1.42 g of 12b, 13-dibromo-2-methyl-2,3,8,12b-tetrahydro-1H-3a,8-methanodibenzo[3,4:6,7]-cyclohepta[1,2-c]pyrrol-1-one, (1a), mp 215°–216° (dec). A sample crystallized from acetonitrile melted at 221°–222° (dec); nmr spectrum: τ 1.6–1.8 (m, 1); 2.3–2.8 (m, 7); 5.1 (d, J = 4.5 Hz, 1); 5.7 (d, J = 10.5 Hz, 1); 5.8 (d, J = 4.5 Hz, 1); 6.6 (d, J = 10.5 Hz, 1) and 6.9 (s, 3).

Anal. Calcd for $C_{19}H_{15}Br_2NO$: C, 52.68; H, 3.49; N, 3.24
Found: C, 52.83; H, 3.43; N, 3.34

A mixture of 8.07 g of 1a, 17.2 g of freshly distilled tributyltin hydride and 50 ml of anhydrous benzene is heated under reflux under nitrogen for 3 days. Most of the benzene is removed and the residue is distilled through a short-path column (to 125° bath temperature, 1 micron). The pot residue is crystallized from isopropyl alcohol to give 3,63 g (71% yield) of 2-methyl-2,3,8,12b-tetrahydro-1H-3a,8-methanodibenzo[3,4:6,7]-cyclohepta[1,2-c]pyrrol-1-one (1b), mp 141°-146°. A sample crystallized once from isopropyl alcohol has mp 147°-157°.

Anal. Calcd for $C_{19}H_{17}NO$: C, 82,88; H, 6.22; N, 5.09
Found: C, 82.31; H, 6.18; N, 5.18.

A mixture of 1.65 g of 1b and 50 ml of 1M diborane in tetrahydrofuran is heated under reflux for 24 hours. To the cooled mixture is added slowly 10 ml of concentrated hydrochloric acid; the tetrahydrofuran is removed under vacuum; concentrated hydrochloric acid (10 ml) is added to the residue, and the mixture is heated under reflux for 7 hours. After concentration to a small volume the mixture is made basic and extracted with methylene chloride. Removal of the solvent from the dried extract gives 1.57 g of an oil, the main constituent of which is 2-methyl-2,3,8,12b-tetrahydro-1H-3a,8-methanodibenzo[3,4:6,7]cyclohepta[1,2-c]pyrrole (1c); nmr spectrum (220 mc): τ 2.6-3.1 (m, 8); 5.9 (d, 4 Hz, 1); 6.0 (d, 10 Hz, 1); 6.3 (t, probably d/d, 1); 6.6 (d/d, 8/10 Hz, 1); 7.0 (d, 10 Hz + additional bands, 2); 7.2 (s, 3); 7.4 (d/d, 10/4 Hz, 1) and 7.5 (d, 10 Hz, 1). The product is converted to the hydrochloride salt which melts at 255°-257° (dec) after crystallization from acetonitrile.
Anals. Calcd for $C_{19}H_{20}ClN$: C, 76,62 H, 6.77; N, 4.70
Found: C, 76.77; H, 6.56; N, 4.70.

The 2-methyl-3,5-dihydro-5,9b-o-benzenobenz[e]-isoindol-1-(2H)-one starting material was prepared as follows: a mixture of 25 g of 9-anthroic acid and 75 ml of thionyl chloride is heated under reflux for 1 hour. The excess thionyl chloride is removed under vacuum (30 mm; 90° bath temperature); 50 ml of toluene is added and the mixture is concentrated again. This operation is repeated once more to give 28.3 g of 9-anthroyl chloride as a very moisture-sensitive, yellow solid.

A solution of 20.8 g of 9-anthroyl chloride in 100 ml of tetrahydrofuran is added at 10°-15° to a solution of 14.2 g of N-methylpropargylamine in 50 ml of tetrahydrofuran. After stirring at room temperature for 3 hours, the solvent is removed and the residue is stirred with methylene chloride and 5% aqueous sodium bicarbonate solution. The methylene chloride layer is dried and concentrated to give 23.3 g of crude N-methyl-N-propargyl-9-anthramide as an oil. H nmr spectrum: τ 1.7-2.9 (m, 9); 5.4 (d, 2.5 Hz, 1.3); 6.4 (d, 2.5 Hz, 0.7); 6.7 (s, 0.9); 7.4 (s, 2.1); 7.7 (t, 2.5 Hz, 0.7) and 8.0 (t, 0.3). The spectrum shows the presence of two rotamers.

A mixture of 23.2 g of crude N-methyl-N-propargyl-9-anthramide and 200 ml of p-xylene is heated under reflux for 2.25 hrs. The solvent is removed and the residue is crystallized from 300 ml of acetonitrile to give 16.4 g of 2-methyl-3,5-dihydro-5,9b-o-benzenobenz[e]-isoindol-1-(2H)-one, mp 250°-255°; nmr spectrum: τ 2.3-3.3 (m, 9); 4.8 (d, J = 6 Hz, 1); 5.9 (d, J = 2 Hz, 2) and 6.9 (s, 3).
Anal. Calcd for $C_{19}H_{15}NO$: C, 83.49; H, 5.53; N, 5.13
Found: C, 83.84; H, 5.66; N, 5.10

EXAMPLE 2

2-Methyl-2,3,8,12b-tetrahydro-1H-3a,8-methanodibenzo[3,4:6,7]cyclohepta[1,2-c]pyrrole by Acid-Catalyzed Rearrangement

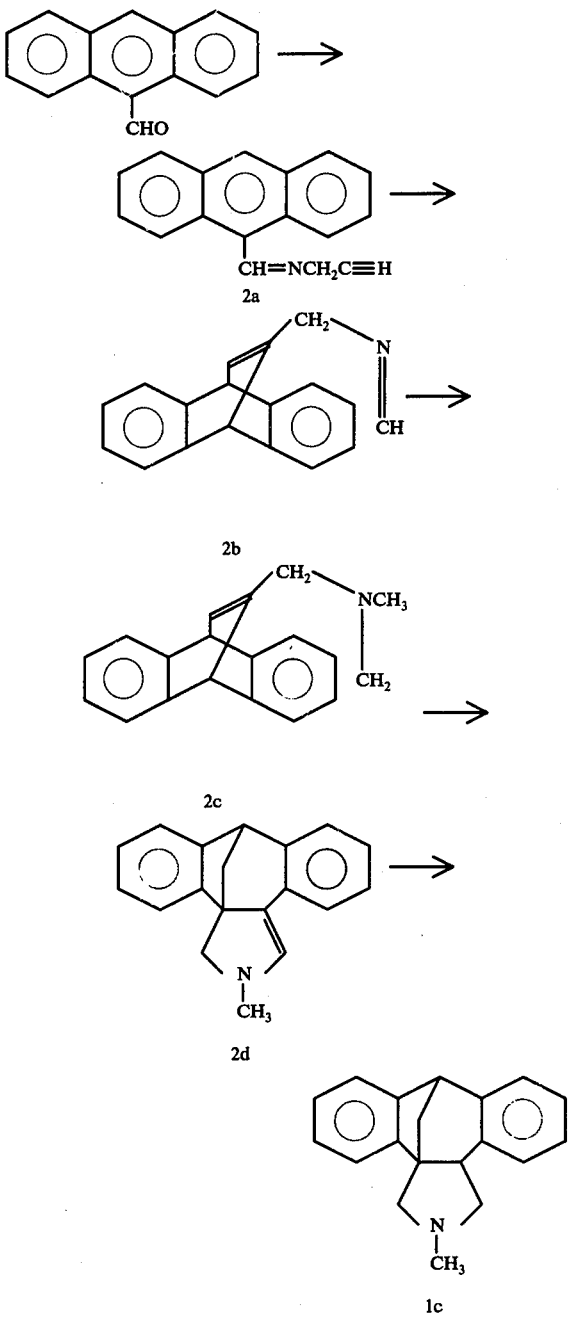

A mixture of 16.7 g of 9-anthraldehyde, 5 g of propargylamine and 100 ml of ethanol is heated under reflux for 1 hour. The solvent is removed and the residue is crystallized from 100 ml of acetonitrile to give 16.1 g (82%) of N-propargyl-9-anthracenemethylenimine; (2a), mp, 143°-144°; nmr spectrum: τ0.2(t, 2 Hz, 1); 1.7-3.0 (m,9); 5.1 (t, 2 Hz, 2) and 7.3 (t, 2 Hz, 1).
Anal. Calcd for $C_{18}H_{13}N$: C, 88.86; H, 5.39; N, 5.76
Found: C, 88.83; H, 5.56; N, 5.87.

A mixture of 19.4 g of crude N-propargyl-9-anthracenemethylenimine and 200 ml of p-xylene is heated under reflux for 3 hours. On cooling, 14.6 g of 3,5-dihydro-5,9-b-o-benzenobenz[e]isoindole (2b), mp, 212°–214°, precipitates. Another 1.4 g of product is obtained by removing the solvent from the mother liquor and crystallizing the residue from 50 ml of acetonitrile; nmr spectrum: τ1.1 (m, 1); 2.5–3.5(m, 9); 4.8 (d, J = 6 Hz, 1) and 5.4 (t, J = 2Hz, 2).

Anal. Calcd for $C_{18}H_{13}N$: C, 88.86; H, 5.39; N, 5.76 Found: C, 89.10; H, 5.58; N, 5.66.

A mixture of 8.19 g of 3,5-dihydro-5,9b-o-benzenobenz[e]isoindole, 25 ml of formic acid and 25 ml of aqueous formaldehyde solution is heated under reflux for 3 hours. Concentrated hydrochloric acid (10 ml) is added, and the volatiles are removed. The residue is stirred with aqueous sodium hydroxide solution and methylene chloride. Removal of the solvent from the dried methylene chloride extracts and crystallization of the residue from acetonitrile gives, in two crops, 5.04 g (58%) of 2-methyl-1,2,3,5-tetrahydro-5,9b-o-benzobenz[e]isoindole (2c), mp 196°–197°; nmr spectrum; τ 2.43–3.1 (m, 8); 3.3 (d of t, J = 6/2 Hz, 1); 4.8 (d, 6 Hz, 1); 6.1 (s, 2); 6.6 (d, 2 Hz, 2) and 7.3 (s, 3).

Anal. Calcd for $C_{19}H_{17}N$; C, 87.99; H, 6.61; N, 5.40 Found: C, 88.05; H, 6.91; N, 5.32.

A sealed Carius tube containing 20.0 g of 2-methyl-1,2,3,5-tetrahydro-5,9b-o-benzenobenz[e]isoindole and 80 ml of trifluoroacetic acid is heated at 150° for 8 hours. The acid is distilled. The residue is dissolved in methylene chloride and the solution is added slowly to a stirred, cooled, excess 15% aqueous sodium hydroxide solution. The layers are separated and the aqeuous phase is extracted once with methylene chloride. Removal of the solvent from the combined dried extracts gives 19.6 g of 2-methyl-2,3-dihydro-8H-3a,8-methanodibenzo[3,4:6,7]-cyclohepta[1,2-c]pyrrole (2d); nmr spectrum; τ 2.5–3.3 (m,8); 3.9 (s, 1); 6.1(d, 10Hz, 1); 6.1 (d, 4 Hz, split further; 1); 6.9 (d, 10 Hz, 1); 7.3 (s, 3) and 7.4–7.9 (AB quartet, J = 9 Hz; the lower-field component is split again by 4 Hz; the high-field component by ca. 1 Hz; 2). A sample crystallized twice from isopropyl alcohol melted at 119.5°–120°.

Anal. Calcd. for $C_{19}H_{17}N$: C, 87.99; H, 6.61; N, 5.40. Found: C, 87.66; H, 6.74; N, 5.45.

The above rearrangement may also be carried out with p-toluenesulfonic acid in acetic acid at 165°.

A mixture of 13.6 g of 2-methyl-2,3-dihydro-8H-3a, 8-methanodibenzo[3,4:6,7]cyclohepta[1,2-c]pyrrole, 100 ml of acetic acid and 2 g of 10% palladium-on-charcoal catalyst is shaken under 40 psi hydrogen pressure at room temperature until the pressure remains constant. The filtered mixture is concentrated, the residue is made basic and extracted several times with methylene chloride. Removal of the solvent from the dried extracts gives 13.7 g of 2-methyl-2,3,8,12b-tetrahydro-1H-3a,8-methanodibenzo[3,4;6,7]-cyclohepta[1,2-c]pyrrole (1c) identical by nmr spectroscopy with the product obtained in Example 1.

The hydrogenation of 2d to give 1c may also be carried out with a platinum catalyst in tetrahydrofuran. When tetrahydrofuran is used as a solvent with a palladium catalyst, some of the steroisomer of 1c is also formed.

The reduction of 2d to give 1c may also be effected with sodium cyanoborohydride in acetic acid-methanol at room temperature.

EXAMPLE 3

2,3,8,12b-Tetrahydro-1H-3a,8-methanodibenzo[3,4:6,7]-cyclohepta[1,2-c]pyrrole

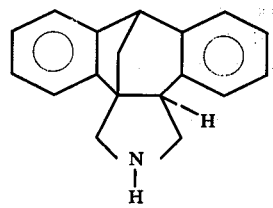

The procedure of Example 1 is employed with 3,5-dihydro-5,9b-o-benzenbenz[e]isoindol-1-(2H)-one replacing its N-methyl homologue. There is obtained 2,3,8,12b-tetrahydro-1H-3a, 8-methanodibenzo[3,4:6,7]-cyclohepta[1,2-c]pyrrole as an oil that slowly forms a solid carbonate on exposure to air. Nmr spectrum: τ 2.6–3.1 (m, 8); 6.0–6.4 (m, 3); 6.5–7.1 (m, 3) and 7.5–8.0 (m, 3). The hydrochloride melts with decomposition at 311°–312°.

Anal. Calcd for $C_{18}H_{18}ClN$: C, 76.18; H, 6.39; N, 4.94. Found: C, 76.60; H, 6.52; N, 4.87.

The starting material is prepared as described for the starting material of Example 1 but replacing N-methylpropargylamine with proparylamine.

2,3,8,12b-Tetrahydro-1H-3a,8-methanodibenzo[3,4:6,7]cyclohepta[1,2-c]pyrrole is preferably prepared by hydrogenolysis of 2-benzyl-2,3,8,12b-tetrahydro-1H-3a,8-methanodibenzo[3,4:6,7]cyclohepta[1,2-c]pyrrole (Examples 4 and 5) with palladium on charcoal in acetic acid at room temperature and about 40 psi hydrogen pressure.

EXAMPLE 4

2-Benzyl-2,3,8,12b-tetrahydro-1H-3a,8-methanodibenzo[3,4:6,7]cyclohepta[1,2-c]pyrrole

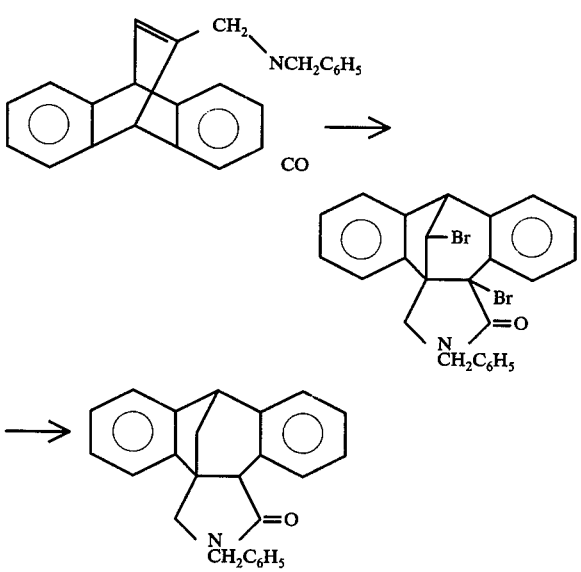

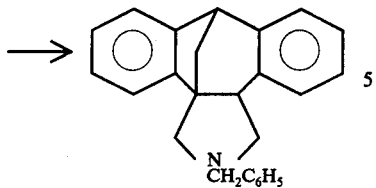

2-Benzyl-3,5-dihydro-5,9b-o-benzenobenz[e]isoindol-1-(2H)-one, prepared as described below, is converted in three steps to 2-benzyl-2,3,8,12b-tetrahydro-1H-3a,8-methanodibenzo[3,4:6,7]cyclohepta[1,2-c]pyrrole using the procedure of Example 1. The free base is obtained as an oil; it has the following nmr spectrum: τ 2.5–3.3 (m, 13) and 6.0–8.0 (m, 10); at 220 MHz, the τ 6.0–8.0 region resolves (from lower to higher field) into a four-proton multiplet a one-proton triplet, a one-proton multiplet, a two-proton multiplet and a two-proton AB quartet (J = 10 Hz) with one component split again (J = 4 Hz).

The starting material is prepared as follows:

To a mixture of 30 ml of benzylamine and 60 ml of tetrahydrofuran is added dropwise with cooling, a solution of 9.86 g of 9-anthroyl chloride in 30 ml of tetrahydrofuran. After stirring at room temperature overnight, the mixture is concentrated, and the residue is dissolved in methylene chloride. The solution is washed with dilute acid and dilute base, dried, and concentrated to give 12.45 g of crude N-benzoyl-9-anthramide. The product is added to a slurry of 2.50 g of sodium hydride (50% in oil, previously washed with hexane) in 80 ml of tetrahydrofuran and the mixture is heated to reflux for 30 min and cooled. Propargyl bromide (6.0 g) in 10 ml of tetrahydrofuran is added, and the reaction mixture is heated under reflux for 2 hours. Water and methylene chloride are added; the layers are separated, and the dried organic layer is concentrated. The residue (crude N-benzyl-N-propargyl-9-anthramide) is heated under reflux with 100 ml of p-xylene for 2.5 hr. On cooling, 9.81 g of 2-benzyl-3,5-dihydro-5,9b-o-benzenobenz [e]-isoindol-1-(2H)-one precipitates.

EXAMPLE 5

2-Benzyl-2,3,8,12b-tetrahydro-1H-3a,8-methanodibenzo[3,4:6,7]cyclohepta[1,2-c]pyrrole by Acid-Catalyzed Rearrangement

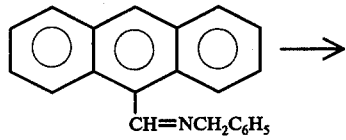

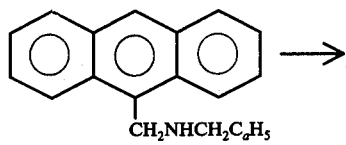

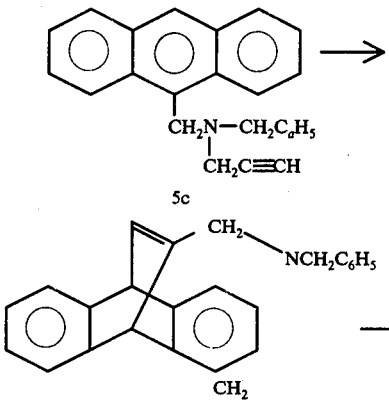

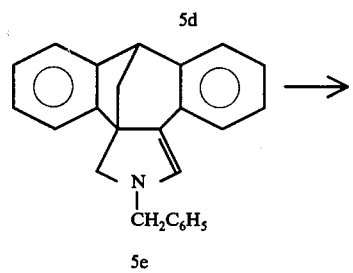

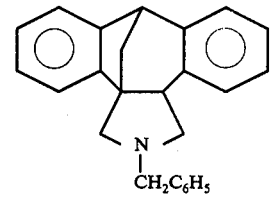

A mixture of 100 g of 9-anthraldehyde, 53 g of benzylamine and 300 ml of ethanol is heated under reflux under nitrogen for 2.5 hours. The solution of N-benzyl-9-anthracenemethylenimine (5a) so obtained is cooled to 60°, and 18.78 g of sodium borohydride is added slowly, keeping the temperature at 60°–65°. After stirring at room temperature overnight the excess hydride is destroyed by the slow addition of conc. hydrochloric acid. This mixture is then made basic and is extracted several times with methylene chloride. Removal of the solvent from the dried extracts gives 139.9 g of N-benzyl-9-anthracenemethylamine (5b). Nmr spectrum: τ 1.8–3.0 (m, 14); 5.5 (s, 2); 6.2 (s, 2) and 8.5 (s, 1).

The product is dissolved in 300 ml of methylene chloride; 200 ml of 10% aqueous potassium carbonate solution and 100 ml of propargyl bromide is added, and the mixture is stirred vigorously under nitrogen at room temperature for 3 hours. The layers are separated, the aqueous layer is extracted once with methylene chloride, the combined extracts are washed with conc. sodium chloride solution, and dried. Removal of the solvent gives 153.5 g of N-benzyl-N-propargyl-9-anthracenemethylamine (5C). Nmr spectrum: τ 1.5–3.0 (m, 14); 5.5 (s, 2); 6.3 (s, 2); 6.9 (d,J=2.5 Hz, 2) and 7.7 (t, J=2.5Hz, 1).

The product is heated under reflux with 1 liter of toluene for 2.25 hours. Removal of the solvent gives crude 2-benzyl-1,2,3,5-tetrahydro-5,9b,o-benzenobenz-[e]isoindole (5d). A sample crystallized from isopropyl alcohol was identical by nmr spectroscopy with the product obtained by benzoylation of 1,2,3,5-tetrahydro-5,9-b-o-benzenobenz[e]isoindole followed by reduction (see below).

A mixture of 48.9 g 2-benzyl-1,2,3,5-tetrahydro-5,9-b-o-benzenobenz[e]isoindole (5d) and 150 ml of trifluoroactic acid, contained in three sealed Carius tubes, is heated at 150° for 12 hours. The excess acid is distilled under vacuum, the residue is dissolved in methylene chloride, and the solution is added slowly to cold, stirred, excess 15% aqueous sodium hydroxide solution. The layers are separated, the aqueous phase is extracted once with methylene chloride, and the combined extracts are dried. Removal of the solvent and crystallization of the residue from 150 ml of acetonitrile gives 38.3 g of 2-benzyl-2,3-dihydro-8H-3a,8-methanodibenzo[3,4:6.7]-cyclohepta[1,2-c]pyrrole (5e). Nmr spectrum: $\tau$ 2.4–3.1 (m, 13); 3.7 (s, 1); 5.7–7.8 (m, 7). An analytical sample, prepared by crystallization from acetonitrile, had m.p. 135°–145°.

Anal. Calcd for $C_{25}H_{21}N$: C, 89.51; H, 6.31; N, 4.18 Found: C, 89.56; H, 6.45; N, 4.46.

A mixture of 37.7 g of finely powdered 2-benzyl-2,3-dihydro-8H-3a, 8-methanodibenzo[3,4:6,7]cyclohepta[1,2-c]pyrrole (5e), 300 ml of methanol, and 40 ml of acetic acid is cooled with ice, and 14.8 g of sodium cyanoborohydride is added slowly with stirring. The mixture is stirred at room temperature for 3 hours, cooled, and treated with 50 ml of conc. hydrochloric acid. After stirring at room temperature for 0.5 hour the mixture is made basic and extracted several times with methylene chloride. Removal of the solvent from the dried extracts gives 37.5 g of 2-benzyl-2,3,8,12b-tetrahydro-1H-3a,8-methanodibenzo[3,4:6,7]-cyclohepta[1,2-c]pyrrole, identical by nmr spectroscopy with the product obtained in Example 4. The hydrochloride melts with decomposition at 195°–200° after crystallization from ethanol.

Anal. Calcd. for $C_{25}H_{24}ClN$: C, 80.30; H, 6.47; N, 3.75 Found: C, 79.92; H, 6.80; N, 4.13.

The intermediate, 2-benzyl-1,2,3,5-tetrahydro-5,9b-o-benzenobenz[e]isoindole (5d) may also be prepared as follows:

To a slurry of 10.19 g of 3,5-dihydro-5,9b-o-benzobenz[e]isoindole (Example 2) in 50 ml of methanol and 10 ml of acetic acid is added slowly, with cooling, 4.70 g of sodium cyanoborohydride. The mixture is stirred at room temperature overnight, the excess hydride is destroyed with concentrated hydrochloric acid (ice bath), and the mixture is made basic and extracted with methylene chloride. Removal of the solvent from the dried extract gives 10.49 g of 1,2,3,5-tetrahydro-5,9b-o-benzenobenz[e]isoindole as an oil; nmr spectrum: $\tau$ 2.6–3.7 (m, 9); 4.9 (d, 6 Hz, 1); 6.0 (s, 2); 6.5 (d, 2 Hz, 2) and 7.5 (s, 1).

To a mixture of 4.60 g of 1,2,3,5-tetrahydro-5,9b-o-benzenobenz[e]isoindole, 5 g of magnesium oxide, and 20 ml of tetrahydrofuran is added 4.19 g of benzoyl chloride. After stirring at room temperature overnight the mixture is filtered, the filtrate is concentrated, and the residue is dissolved in methylene chloride. The solution is washed in turn, with 10% potassium carbonate solution and water, and the solvent is removed. The residue, crude 2-benzoyl-1,2,3,5-tetrahydro-5,9b-o-benzenobenz[e]isoindole, is heated under reflux with 2.83 g of lithium aluminum hydride in tetrahydrofuran for 4 hours. To the cooled mixture is added slowly 2.8 ml of water, followed by 2.8 ml of 15% aqueous sodium hydroxide solution, and finally 8.4 ml of water. The mixture is filtered, and the filtrate is concentrated to give 5.45 g of crude 2-benzyl-1,2,3,5-tetrahydro-5,9b-o-benzenobenz[e]isoindole (5d). Crystallization of 1.06 g of this material from isopropyl alcohol gives 0.66 g of pure 5d, m.p. 125°–126°, nmr spectrum, $\tau$ 2.4–3.6 (m, 14); 5.0 (d, 6Hz, 1); 6.2 (s, 2); 6.3 (s, 2) and 6.7 (d, 2Hz, 2).

Anal. Calcd for $C_{25}H_{21}N$: C, 89.51; H, 6.31; N, 4.18. Found: C, 89.77; H, 6.26; N, 4.26.

EXAMPLE 6

2-Cyclopropylmethyl-2,3,8,12b-tetrahydro-1H-3a,8-methanodibenzo[3,4:6,7]cyclohepta[1,2-c]pyrrole

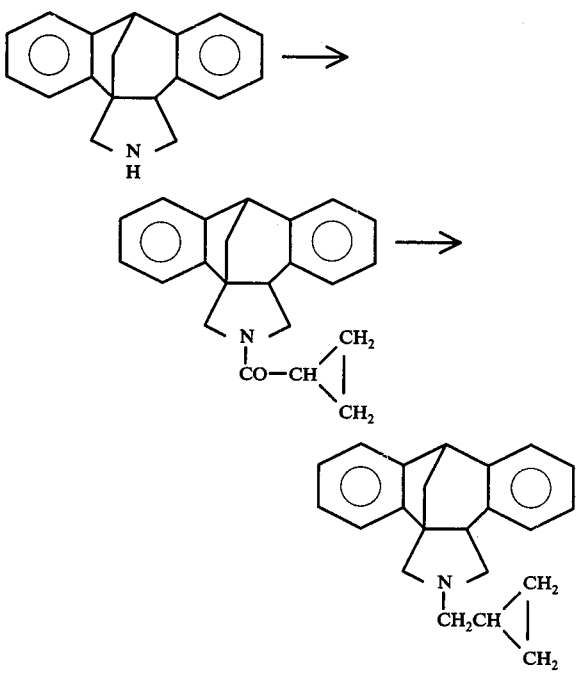

To a slurry of 1.34 g of 2,3,7,12b-tetrahydro-1H-3a,8-methanodibenzo[3,4:6,7]cyclohepta[1,2-c]pyrrole Example 3) and 3 g of magnesium oxide is added 0.93 g of cyclopropanecarbonyl chloride, and the mixture is stirred at room temperature overnight. The filtered mixture is concentrated; the residue is dissolved in methylene chloride, and the solution is washed with base, dried, and concentrated. The residue is heated under reflux with 0.57 g of lithium aluminum hydride in tetrahydrofuran overnight. To the cooled mixture is added, in turn, 0.6 ml of water, 0.6 ml of 15% aqueous sodium hydroxide solution, and 1.8 ml of water; the mixture is filtered, and the filtrate is concentrated to give 1.35 g of 2-cyclopropylmethyl-2,3,8,12b-tetrahydro-1H-3a, 8-methanodibenzo[3,4:6,7]cyclohepta[1,2-c]pyrrole as an oil; nmr spectrum: $\tau$ 2.7–3.2 (m, 8); 6.0–8.0 (m, 8) and 8.8–10.0 (m, 5). It is converted to the hydrochloride which is crystallized from isopropyl alcohol. The melting point of the hydrochloride is erratic and depends upon the rate of heating. Extending drying of the hydrochloride at 120°–130° for 8 hours at 0.1 micron gives a solvent-free product, m.p. 251°–252°, with decomposition.

Anal. Calc'd. for $C_{22}H_{24}ClN$: C, 78.20; H, 7.16; N, 4.14 Found: C, 78.01; H, 6.91; N, 4.50.

EXAMPLE 7

2-Cyclopentylmethyl-2,3,8,12b-tetrahydro-1H-3a,8-methanodibenzo[3,4:6,7]cyclohepta[1,2-c]pyrrole by Acylation of 2,3,8,12b-Tetrahydro-1H-3a,8-methanodibenzo[3,4:6,7]cyclohepta[1,2-c]pyrrole Followed by Reduction

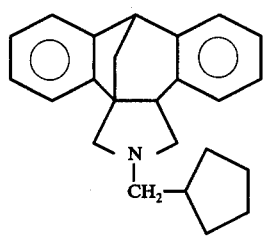

Following the procedure of Example 6, but using cyclopentanecarbonyl chloride in place of cyclopropanecarbonyl chloride there is obtained 2-cyclopentylmethyl-2,3,8,12b-tetrahydro-1H-3a,8-methanodibenzo[3,4:6,7]cyclohepta[1,2-c]pyrrole as an oil that slowly crystallizes. Nmr spectrum: $\tau$ 2.5–3.0 (m, 8) and 6.0–9.0 (M, 19); at 220 MHz the $\tau$ 6.0–9.0 area resolves, from low to high field, into a doublet (J = 4 Hz, 1) a doublet (J = 10 Hz, 1); a doublet of doublets (J ≈ 7 and 8 Hz; 1); a doublet of doublets (J = 7 and 11 Hz; 1); a four-proton multiplet; a doublet of doublets (J = 4 and 10 Hz, 1); a doublet (J = 10 Hz; 1) and multiplets (1, 2, 4, and 2 protons). The hydrochloride melts with decomposition at 250°–253° after crystallization from isopropyl alcohol and drying at 110°–115° under 0.2 micron pressure for 9 hours.

Anal. Calcd. for $C_{24}H_{28}ClN$: C, 78.77; H, 7.71; N, 3.83 Found: C, 78.52; H, 7.83; N, 3.72.

The N-Oxide of 2-cyclopentylmethyl-2,3,8,12b-tetrahydro-1H-3a,8-methanodibenzo[3,4:6,7]cyclohepta[1,2-c]-pyrrole is prepared as follows: A solution of 3.92 g of the free base in 20 ml of chloroform is added slowly to a cooled mixture of 10 ml of 40% peracetic acid and 2 g of anhydrous sodium acetate. The mixture is stirred at room temperature for 90 minutes, cooled, and made basic by the addition of 15% aqueous sodium hydroxide solution. The layers are separated and the aqueous phase is extracted once with chloroform. The combined organic phases are dried and concentrated to give 3.80 g of crude product still retaining some solvent; the nmr spectrum indicates the presence of two isomers. Addition of hot ethyl acetate causes one isomer to crystallize; it is purified by recrystallization from acetonitrile; nmr spectrum (220 MHz) from low to high field: aromatic region $\tau$ 2.3–3.3 (d, J = 7.5 Hz, 1 and m, 7); aliphatic region, $\tau$ 5.5–9.0 (m, 2; d, J = 4.5 Hz + m, 2; d, J = 12 Hz, 1; m, 3; m, 1; d/d, J = 4.5/10 Hz, 1; d, J = 10 Hz + m, 3; m, 4 and m, 2).

2-Cyclopentylmethyl-2,3,8,12b-tetrahydro-trans-1H,-3a,8-methanodibenzo[3,4:6,7]cyclohepta[1,2-c]pyrrole is resolved into its optical antipodes by fractional crystallization of the (+) and (−) dibenzoyl (−) tartaric acid salts. The hydrochloride of the (+) isomer has $[\alpha]_D = +125°$ (c=2.21 g/100 ml of chloroform); the hydrochloride of the (−) isomer has $[\alpha]_D = -125°$ (c=2.00 g/100 ml of chloroform).

EXAMPLE 8

2-Cyclopentylmethyl-2,3,8,12b-tetrahydro-1H-3a,8-methanodibenzo[3,4:6,7]cyclohepta[1,2-c]pyrrole by Acid-Catalyzed Rearrangement of 2-Cyclopentylmethyl-1,2,3,5-tetrahydro-5,9b,o-benzenobenz[e]isoindole

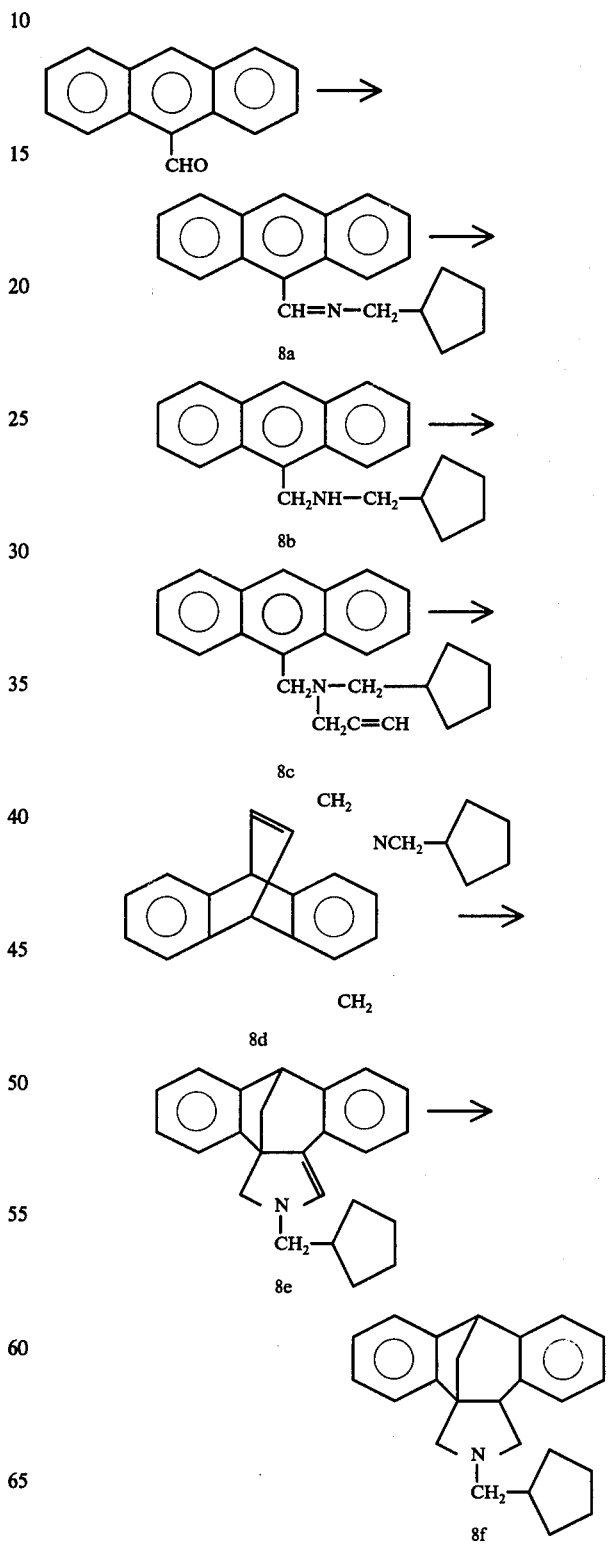

Following the procedure of Example 5, but using cyclopentylmethylamine in place of benzylamine there is obtained, in turn:

N-cyclopentylmethyl-9-anthracenemethyleneimine (8a); nmr spectrum: τ 0.9 (t, 1); 1.5–2.8 (m, 9); 6.3 (d, split further, 2) and 7.3–9.0 (m, 9).

N-Cyclopentylmethyl-9-anthracenemethylamine (8b); nmr spectrum: τ 1.8–3.1 (m, 9); 5.6 (s, 2); 7.5 (d, 7 Hz, 2) and 7.8–9.3 (m, 10).

N-Cyclopentylmethyl-N-propargyl-9-anthracenemethylamine (8c); nmr spectrum: τ 2.3–3.0 (m, 9); 5.5 (s, 2); 6.8 (d, 2.5 Hz, 2); 7.5 (m, 2); 7.7 (t, 2.5 Hz, 1) and 7.5–9.2 (m, 9).

2-Cyclopentylmethyl-1,2,3,5-tetrahydro-5,9b-o-benzenobenz[e]isoindole (8d); m.p. 110°–111°; nmr spectrum: τ 2.6–3.2 (m, 8); 3.5 (d/t, 6/2 Hz, 1); 4.9 (d, 6 Hz, 1); 6.2 (s, 2); 6.7 (d, 2 Hz, 2) and 7.3–9.0 (m, 11).
Anal. Calcd for C$_{24}$H$_{25}$N: C, 88.03; H, 7.70; N, 4.28. Found: C, 87.68; H, 7.75; N, 4.43.

2-Cyclopentylmethyl-2,3-dihydro-8H-3a,8-methanodibenzo[3,4:6,7]cyclohepta[1,2-c]pyrrole (8e), m.p. 103°–104°; nmr spectrum: τ 2.6–3.3 (m, 8); 3.9 (s, 1); 6.0–6.3 (d, 4 Hz, 1 and d, 10 Hz, 1); 6.8 (d, 10 Hz, 1) and 7–9 (m, 13).
Anal. Calcd. for C$_{24}$H$_{25}$N: C, 88.03; H, 7.70; N, 4.28. Found: C, 87.83; H, 8.06; N, 4.34.

2-Cyclopentylmethyl-2,3,8,12b-tetrahydro-1H-3a,8-methanodibenzo[3,4:6,7]cyclohepta[1,2-c]pyrrole (8f), identical by 220 Mhz nmr spectroscopy with the product of Example 7. The reduction of 8e to 8f may be carried out with hydrogen in acetic acid using palladium on charcoal as the catalyst as described in Example 2.

EXAMPLE 9

2-Cyclopentylmethyl-2,3,8,12b-tetrahydro-1H-3a,8-methanodibenzo[3,4:6,7]cyclohepta[1,2-c]pyrrole Via Acid-Catalyzed Rearrangement of 2-Cyclopentanecarbonyl-1,2,3,5-tetrahydro-5,9b-o-benzenobenz[e]isoindole

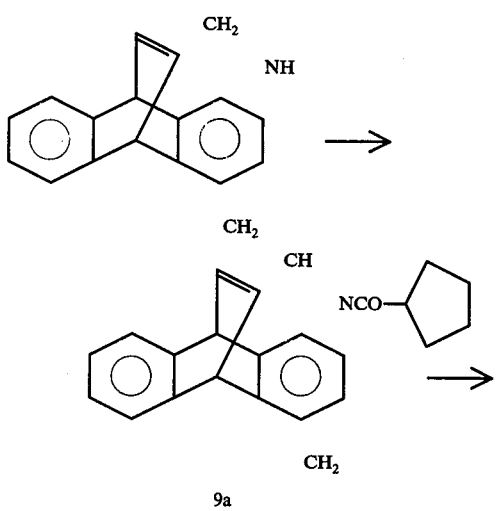

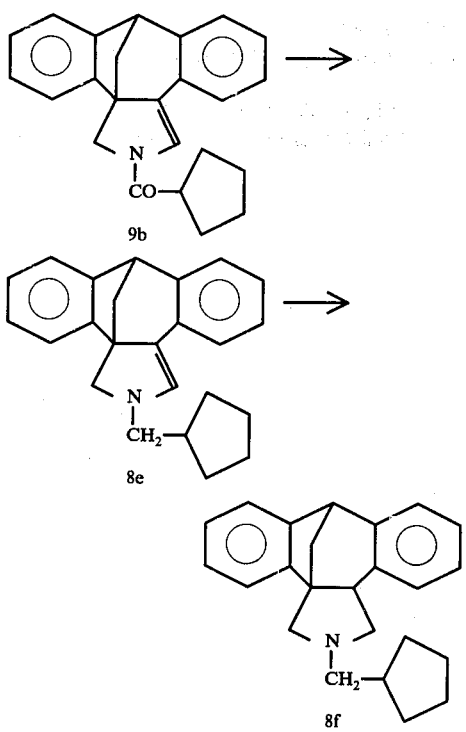

A mixture of 12.07 g of 1,2,3,5-tetrahydro-5,9b-o-benzenobenz[e]isoindole (Example 5), 70 ml of chloroform, and 35 ml of triethylamine is treated with 10.5 g of cyclopentanecarbonyl chloride, keeping the temperature below 20°. After stirring at room temperature for 2 hours, 10% aqueous sodium hydroxide solution is added with cooling, and the mixture is stirred at room temperature for 30 minutes. The layers are separated, and the aqueous phase is extracted once with methylene chloride. Removal of the solvent from the dried extracts and crystallization of the residue from 50 ml of acetonitrile gives 13.14 g of 2-cyclopentanecarbonyl-1,2,3,5-tetrahydro-5,9b-o-benzenobenz[e]isoindole (9a). Nmr spectrum: 2.5–3.5 (m, 9); 4.8 (d, 6 Hz, 1); 5.1 (s, 2); 5.8 (d, 2 Hz, 2) and 6.7–8.7 (m, 9). An analytical sample (acetonitrile) had m.p. 189°–190°.
Anal. Calcd. for C$_{24}$H$_{23}$NO: C, 84.42; H, 6.79; N, 4.10 Found: C, 84.04; H, 6.79; N, 4.29.

A mixture of 11.67 g of the above product and 60 ml of trifluoroacetic acid is heated under reflux for 2 hours. The excess acid is removed under vacuum, the residue is dissolved in methylene chloride and the solution is poured into cold, stirred, excess aqueous sodium hydroxide solution. The mixture is extracted several times with methylene chloride, the extracts are dried, the solvent is removed and the residue is crystallized from 40 ml of toluene to give 10.89 g of 2-cyclopentanecarbonyl-2,3-dihydro-8H-3a,8-methanodibenzo[3,4:6,7]cyclohepta[1,2-c]pyrrole (9b), nmr spectrum: τ 2.5–3.2 (m, 9); 5.0–6.1 (m, 3) and 6.6–8.5 (m, 11). An analytical sample (acetonitrile) had m.p. 185°–186°.
Anal. Calcd. for C$_{24}$H$_{23}$NO: C, 84.42; N, 6.79; N, 4.10. Found: C, 84.60; H, 6.93; N, 4.55.

To a cooled slurry of 0.40 g of lithium aluminum hydride in 30 ml of ether is added 1.55 g of 9b and the mixture is stirred at room temperature for 6 hours. The excess hydride is decomposed by the addition of 0.4 ml of water, followed by 0.4 ml of 15% aqueous sodium hydroxide solution and 1.2 ml of water. The mixture is filtered and the filtrate is concentrated. Crystallization of the residue from isopropyl alcohol gives 0.89 g of 2-cyclopentylmethyl-2,3-dihydro-8H-3a,8-methanodibenzo[3,4:6,7]cyclohepta[1,2-c]pyrrole (8e), identical by infrared and nmr spectroscopy with the product obtained in Example 8. Reduction of 8e as described in Example 8 gives 2-cycopentylmethyl-2,3,8,12b-tetrahydro-1H-3a,8-methanodibenzo[3,4:6,7]-cyclohepta[1,2-c]pyrrole.

When 2-cyclopentanecarbonyl-2,3-dihydro-8H-3a,8-methanodibenzo[3,4:6,7]cyclohepta[1,2-c]pyrrole (9b) is hydrogenated with palladium-on-carbon catalyst in tetrahydrofuran, 2-cyclopentanecarbonyl-2,3,8,12b-tetrahydro-1H-3a, 8-methanodibenzo[3,4:6,7]cyclohepta[1,2-c]pyrrole having the cis sterochemistry at the 3a–12b-ring fusion is formed.

EXAMPLE 10

2-Allyl-2,3,8,12b-tetrahydro-1H-3a,8-methanodibenzo-[3,4:6,7]cyclohepta[1,2-c]pyrrole.

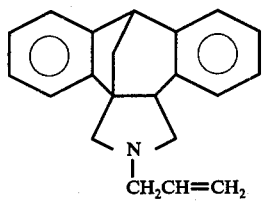

A mixture of 2.19 g of 2,3,8,12b-tetrahydro-1H-3a,-8-methanodibenzo[3,4:6,7]cyclohepta[1,2-c]pyrrole (Example 3), 20 ml of chloroform, 20 ml of 10% aqueous potassium carbonate solution and 4 ml of allyl bromide is stirred vigorously under nitrogen at room temperature for 5 hours. A precipitate formed is brought into solution by addition of methanol; the layers are separated and the aqueous phase is extracted once with a mixture of methylene chloride and methanol. The solvent is removed from the dried extracts and the residue is heated with 15 ml of methanol and 6 g of trimethylamine in a sealed Carius tube at 110° for 8 hours; this treatment converts any quaternary salt to the desired tertiary amine. The solvent is removed and the residue is dissolved in methylene chloride. The solution is washed with aqueous sodium hydroxide solution and dried. Removal of the solvent gives 2-allyl-2,3,8,12b-tetrahydro-1H-3a,8-methanodibenzo[3,4:6,7]cyclohepta[1,2-c]pyrrole. The hydrochloride, after crystallization from isopropyl alcohol, weighed 1.60 g; m.p. 208°–209° (dec.)

Anal. Calcd. for $C_{21}H_{22}ClN$: C, 77.88; H, 6.85; N, 4.33 Found: C, 78.14; H, 7.02; N, 4.47.

The free base has the following nmr spectrum: $\tau$ 2.7–3.2 (m, 8); 3.7–4.4 (m, 1); 4.6–5.1 (m, 2) and 6.1–7.9 (m, 10).

EXAMPLE 11

Ethyl 2,3,8,12b-Tetrahydro-1H-3a,8-methanodibenzo-[3,4:6,7]cyclohepta[1,2-c]pyrrole-2-butyrate

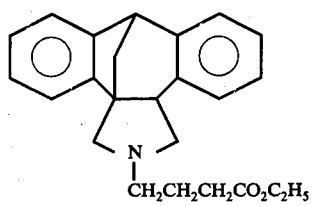

A mixture of 2.35 g of 2,3,8,12b-tetrahydro-1H-3a,8-methanodibenzo[3,4:6,7]cyclohepta[1,2-c]pyrrole, 25 ml of dimethylformamide, 4 ml of triethylamine and 2.55 g of ethyl 4-bromobutyrate is heated at 60°–65° bath temperature under nitrogen for 18 hours. The cooled reaction mixture is diluted with water and extracted twice with methylene chloride. The extracts are washed with dilute aqueous sodium hydroxide solution, dried and concentrated to give 3.07 g of crude ethyl 2,3,8,12b-tetrahydro-1H,3a,8-methanodibenzo[3,4:6,7]-cyclohepta[1,2-c]pyrrole-2-butyrate. Nmr spectrum: $\tau$ 2.7–3.2 (m, 8); 5.9 (quartet J = 7 Hz, 2); 6.0–8.5 (m, 14) and 8.8 (t, 7 Hz, 3).

The following derivatives of 2,3,8,12b-tetrahydro-1H-3a,8-methanodibenzo[3,4:6,7]cyclohepta[1,2-c]pyrrole have been prepared according to the procedures outlined in the preceding Examples. For the purpose of identification, these procedures are designated:

(I) Acylation of 2,3,8,12b-tetrahydro-1H-3a,8-methanodibenzo[3,4:6,7]cyclohepta[1,2-c]pyrrole with the appropriate acid chloride followed by reduction (Example 6).

(II) Reaction of 9-anthraldehyde, optionally substituted in the benzene ring(s), with an appropriate primary amine, followed by the steps outlined in Example 5.

(III) Reaction of 9-anthroyl chloride with an appropriately N-substituted propargylamine followed by the steps outlined in Example 1.

(IV) Alkylation of 2,3,8,12b-tetrahydro-1H-3a,8-methanodibenzo[3,4:6,7]cyclohepta[1,2-c]pyrrole (Examples 10 and 11).

EXAMPLE 12

2-Ethyl-2,3,8,12b-tetrahydro-1H-3a,8-methanodibenzo[3,4:6,7]cyclohepta[1,2-c]pyrrole; method I; nmr spectrum: $\tau$ 2.5–3.2 (m, 8); 6.0–8.0 (m, 10), and 8.8 (t, 3).

EXAMPLE 13

2-n-Butyl-2,3,8,12b-tetrahydro-1H-3a,8-methanodibenzo[3,4:6,7]cyclohepta[1,2-c]pyrrole; method I; nmr spectrum: $\tau$ 2.7–3.2 (m, 8) and 6.1–9.3 (m, 17).

EXAMPLE 14:

2-n-Hexyl-2,3,8,12b-tetrahydro-1H-3a,8-methanodibenzo[3,4:6,7]cyclohepta[1,2-c]pyrrole; method I; nmr spectrum: $\tau$ 2.7–3.2 (m, 8) and 6.0–9.4 (m, 21).

EXAMPLE 15:

2-n-Heptyl-2,3,8,12b-tetrahydro-1H-3a,8-methanodibenzo[3,4:6,7]cyclohepta[1,2-c]pyrrole;

method I; nmr spectrum: τ 2.6–3.1 (m, 8) and 6.0–9.4 (m, 23).

EXAMPLE 16:

2-n-Octyl-2,3,8,12b-tetrahydro-1H-3a,8-methanodibenzo[3,4:6,7]cyclohepta[1,2-c]pyrrole; method I; nmr spectrum: τ 2.6–3.2 (m, 8) and 6.0–9.3 (m, 25).

EXAMPLE 17:

2-(2-Ethylbutyl)-2,3,8,12b-tetrahydro-1H-3a,8-methanodibenzo[3,4:6,7]cyclohepta[1,2-c]pyrrole; method I; nmr spectrum: τ 2.7–3.2 (m, 8) and 6.1–9.2 (m, 21).

EXAMPLE 18:

2-Propargyl-2,3,8,12b-tetrahydro-1H-3a,8-methanodibenzo[3,4:6,7]cyclohepta[1,2-c]pyrrole; method IV; nmr spectrum: τ 2.5–3.1 (m, 8) and 6.0–7.8 (m, 11).

EXAMPLE 19:

2-Cyclobutylmethyl-2,3,8,12b-tetrahydro-1H-3a,8-methanodibenzo[3,4:6,7]cyclohepta[1,2-c]pyrrole; method I; Hydrochloride: mp~260° (dec.); Anal. Calcd. for $C_{23}H_{28}ClN$: C, 78.49; H, 7.45; N, 3.98. Found: C, 78.31; H, 7.31; N, 3.93.

EXAMPLE 20:

2-(3-Methylenecyclobutylmethyl)-2,3,8,12b-tetrahydro-1H-3a,8-methanodibenzo[3,4:6,7]cyclohepta[1,2-c]pyrrole; method I; nmr spectrum: τ 2.7–3.3 (m, 8); 5.2–5.5 (m, 2); and 6.1–8.0 (m, 15).

EXAMPLE 21:

2-(1-Cyclopentenylmethyl)-2,3,8,12b-tetrahydro-1H-3a,8-methanodibenzo[3,4:6,7]cyclohepta[1,2-c]pyrrole; method I; nmr spectrum: τ 2.7–3.2 (m, 8); 4.3–4.5 (m, 1) and 6.0–8.3 (m, 16).

EXAMPLE 22:

2-(2-Cyclopentylethyl)-2,3,8,12b-tetrahydro-1H-3a,8-methanodibenzo[3,4:6,7]cyclohepta[1,2-c]pyrrole; method I; hydrochloride: mp 246°–248° (dec.); Anal. Calcd. for $C_{25}H_{30}ClN$: C, 79.02; H, 7.96; N, 3.69. Found: C, 78.83; H, 7.87; N, 3.55.

EXAMPLE 23:

2-(2-Cyclopent-2-enylethyl)-2,3,8,12b-tetrahydro-1H-3a,8-methanodibenzo[3,4:6,7]cyclohepta[1,2-c]pyrrole; method I, nmr spectrum: τ 2.7–3.1 (m, 8); 4.2–4.4 (m, 2) and 6.0–9.0 (m, 17).

EXAMPLE 24:

2-(3-Cyclopentylpropyl)-2,3,8,12b-tetrahydro-1H-3a,8-methanodibenzo[3,4:6,7]cyclohepta[1,2-c]pyrrole; method I; hydrochloride: mp. 242°–243° (dec.): Anal. Calcd for $C_{26}H_{32}ClN$: C, 79.26; H, 8.19; N, 3.56 Found: C, 79.83; H, 8.33; N, 3.51.

EXAMPLE 25:

2-Cyclohexylmethyl-2,3,8,12b-tetrahydro-1H-3a,8-methanodibenzo[3,4:6,7]cyclohepta[1,2-c]pyrrole; method I, III. Hydrochloride: mp 248°–253° (dec.): Anal. Calcd. for $C_{25}H_{30}ClN$: C, 79.02; H, 7.96; N, 3.69. Found: C, 78.69; H, 7.91; N, 3.79.

EXAMPLE 26:

2-(1-Cyclohexenylmethyl)-2,3,8,12b-tetrahydro-1H-3a,8-methanodibenzo[3,4:6,7]cyclohepta[1,2-c]pyrrole; method I; nmr spectrum: τ 2.7–3.2 (m, 8); 4.0 (m, 1) and 5.5–8.6 (m, 18).

EXAMPLE 27:

2-(3-Cyclohexenylmethyl)-2,3,8,12b-tetrahydro-1H-3a,8-methanodibenzo[3,4:6,7]cyclohepta[1,2-c]pyrrole; method I; nmr spectrum: τ 2.6–3.1 (m, 8); 4.3 (m, 2) and 6.0–9.0 (m, 17).

EXAMPLE 28:

2-(1,4-Cyclohexadienylmethyl)-2,3,8,12b-tetrahydro-1H-3a,8-methanodibenzo[3,4:6,7]cyclohepta[1,2-c]pyrrole; method I; nmr spectrum: τ 2.6–3.1 (m, 8); 4.1–4.5 (m, 3) and 6.0–7.8 (m, 14).

EXAMPLE 29:

2-(2-Cyclohexylethyl)-2,3,8,12b-tetrahydro-1H-3a,8-methanodibenzo[3,4:6,7]cyclohepta[1,2-c]pyrrole; method I; hydrochloride: mp. 234°–238° (dec.);
Anal. Calcd. for $C_{26}H_{32}ClN$: C, 79.26; H, 8.18; N, 3.56 Found: C, 78.77; H, 8.26; N, 3.40.

EXAMPLE 30:

2-(3-Cyclohexylpropyl)-2,3,8,12b-tetrahydro-1H-3a,8-methanodibenzo[3,4:6,7]cyclohepta[1,2-c]pyrrole; method I; nmr spectrum: τ 2.5–3.1 (m, 8) and 6.0–9.5 (m, 25).

EXAMPLE 31:

2-(4-Cyclohexylbutyl)-2,3,8,12b-tetrahydro-1H-3a,8-methanodibenzo[3,4:6,7]cyclohepta[1,2-c]pyrrole; method I; nmr spectrum: τ 2.7–3.2 (m, 8); and 6.1–9.7 (m, 27).

EXAMPLE 32:

2-Cycloheptylmethyl-2,3,8,12b-tetrahydro-1H-3a,8-methanodibenzo[3,4:6,7]cyclohepta[1,2-c]pyrrole; method I; hydrochloride: mp. 254°–256° (dec.)
Anal. Calcd for $C_{26}H_{32}ClN$: C, 79.26; H, 8.19; N, 3.56 Found: C, 79.00; H, 7.86; N, 3.81.
The nmr spectrum of the free base, obtained as an oil, showed bands at τ 2.5–3.2 (m, 8) and 6.0–9.2 (m, 23).

EXAMPLE 33:

2-(4-Cycloheptenylmethyl)-2,3,8,12b-tetrahydro-1H-3a,8-methanodibenzo[3,4:6,7]cyclohepta[1,2-c]pyrrole; method I; nmr spectrum: τ 2.7–3.1 (m, 8); 4.0–4.5 (m, 2) and 6.0–9.3 (m, 19).

EXAMPLE 34:

2-Cyclooctylmethyl-2,3,8,12b-tetrahydro-1H-3a,8-methanodibenzo[3,4:6,7]cyclohepta[1,2-c]pyrrole; method I; nmr spectrum: τ 2.7–3.3 (m, 8) and 6.1–9.2 (m, 25).

EXAMPLE 35:

2-(2-Exo-bicyclo[2.2.1]heptylmethyl)-2,3,8,12b-tetrahydro-1H-3a,8-methanodibenzo[3,4:6,7]cyclohepta[1,2-c]pyrrole; method I; nmr spectrum: τ 2.6–3.1 (m, 8) and 6.0–9.2 (m, 21).

EXAMPLE 36:

2-(2-Endo-bicyclo[2.2.1]heptylmethyl)-2,3,8,12b-tetrahydro-1H-3a,8-methanodibenzo[3,4:6,7]cyclohepta[1,2-c]pyrrole; method I; nmr spectrum: τ 2.6–3.1 (m, 8) and 6.0–9.3 (m, 21).

EXAMPLE 37:

2-(2-Exo-bicyclo[2.2.1]hept-5-enylmethyl)-2,3,8,12b-tetrahydro-1H-3a,8-methanodibenzo[3,4:6,7]cyclohepta[1,2-c]pyrrole; method I; nmr spectrum: τ 2.6–3.2 (m, 8); 3.8–4.1 (m, 2) and 6.0–8.9 (m, 17).

EXAMPLE 38:

2-(2-Endo-bicyclo[2.2.1]hept-5-enylmethyl)-2,3,8,12b-tetrahydro-1H-3a,8-methanodibenzo[3,4:6,7]-cyclohepta[1,2-c]pyrrole; method I; nmr spectrum: τ 2.6–3.3 (m, 8); 3.8–4.2 (m, 2) and 6.1–9.6 (m, 17).

EXAMPLE 39:

2-(2-Phenylethyl)-2,3,8,12b-tetrahydro-1H-3a,8-methanodibenzo[3,4:6,7]cyclohepta[1,2-c]pyrrole; method I; hydrochloride: mp 248°–250° (dec.);

Anal. Calcd. for $C_{26}H_{26}ClN$: C, 80.49; H, 6.76; N, 3.61. Found: C, 80.71; H, 6.82; N, 3.59.

The nmr spectrum of the free base, obtained as an oil, showed bands at τ 2.6–3.2 (m, 13) and 6.0–7.9 (m, 12).

EXAMPLE 40:

2-(2-Phenoxyethyl)-2,3,8,12b-tetrahydro-1H-3a,8-methanodibenzo[3,4:6,7]cyclohepta[1,2-c]pyrrole; method I; nmr spectrum: τ 2.6–3.3 (m, 13) and 5.7–8.3 (m, 12).

EXAMPLE 41:

2-(2-Methoxyethyl)-2,3,8,12b-tetrahydro-1H-3a,8-methanodibenzo[3,4:6,7]cyclohepta[1,2-c]pyrrole; method I; nmr spectrum: τ 2.7–3.1 (m, 8) and 6.1–7.9 (m, 15).

EXAMPLE 42:

2-(2-Furylmethyl)-2,3,8,12b-tetrahydro-1H-3a,8-methanodibenzo[3,4:6,7]cyclohepta[1,2-c]pyrrole; method I; nmr spectrum: τ 2.6–3.2 (m, 9); 3.6–3.9 (m, 2) and 6.0–8.0 (m, 10).

EXAMPLE 43:

5- and 11-Chloro-2-methyl-2,3,8,12b-tetrahydro-1H-3a,8-methanodibenzo[3,4:6,7]cyclohepta[1,2-c]pyrrole; method II; nmr spectrum: τ 2.6–3.2 (m, 7) and 5.9–7.8 (m, 11).

EXAMPLE 44:

5- and 11-Chloro-2-cyclohexylmethyl-2,3,8,12b-tetrahydro-1H-3a,8-methanodibenzo[3,4:6,7]cyclohepta[1,2-c]pyrrole; method II; nmr spectrum: τ 2.5–3.1 (m, 7) and 6.0–9.5 (m, 21).

EXAMPLE 45

2-Cyclohexylmethyl-2,3,8,12b-tetrahydro-1H-3a,8-methanodibenzo[3,4:6,7]cyclohepta[1,2-c]pyrrole

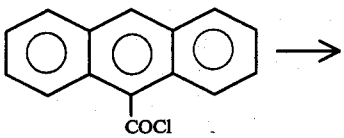

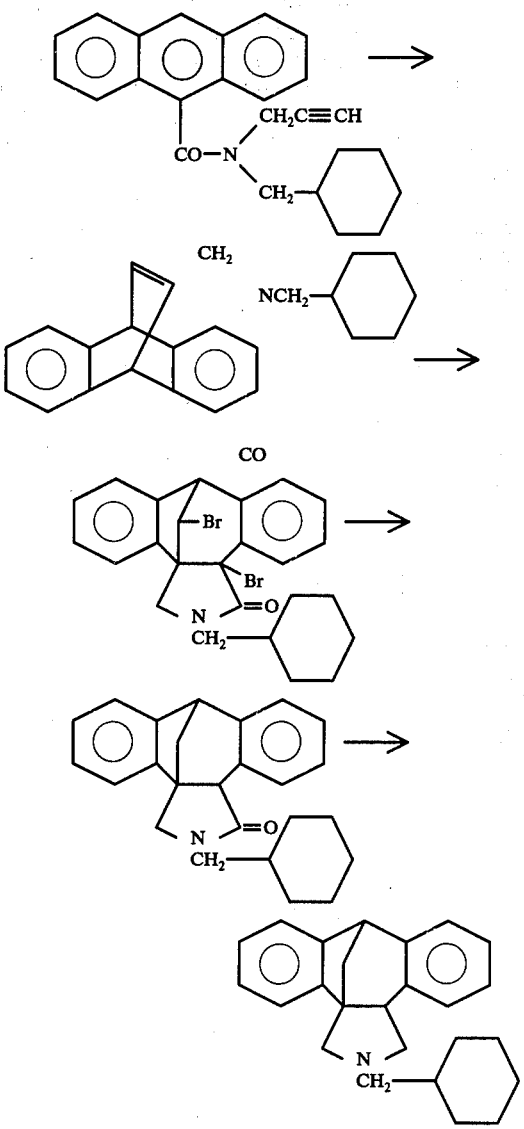

A solution of 12.66 g of 9-anthroyl chloride in 50 ml of tetrahydrofuran is added dropwise to a stirred mixture of 8.69 g of N-propargylcyclohexylmethylamine and 9 g of magnesium oxide in 80 ml of tetrahydrofuran. After stirring at room temperature overnight, the mixture is filtered and the filtrate is concentrated to dryness. The residue is taken up in methylene chloride and washed, in turn, with dilute sulfuric acid, water, and dilute sodium hydroxide solution, and dried. Removal of the solvent gives 14.7 g of N-cyclohexylmethyl-N-propargyl-9-anthramide as an oil. It is dissolved in 100 ml of p-xylene and the mixture is heated under reflux for three hours. The solvent is removed, and the residue is heated under reflux with 60 ml of tetrahydrofuran and 60 ml of 15% aqueous sodium hydroxide solution for one hour. The mixture is concentrated to a small volume, diluted with water and filtered. The solid is washed with dilute alkali and water, dried, and crystallized from toluene to give 6.68 g of 2-cyclohexylmethyl-3,5-dihydro-5,9b-o-benzenobenz[e]isoindol-1(2H)-one; nmr spectrum: τ 2.3–3.4 (m, 9); 4.8 (d, J = 6Hz, 1) 5.9 (d, J = 2Hz, 2); 6.6 (d, J = 6.5 Hz, 2) and 8.0–9.2 (m, 11).

The above product (2.94 g) is treated with 1.41 g of bromine in methylene chloride at room temperature. The resulting crude 12b,13-dibromo-2-cyclohexylmethyl-2,3,8,12b-tetrahydro-1H-3a,8-methanodibenzo[3,4:6,7]cyclohepta[1,2-c]pyrrol-1-one is heated under reflux with 9 g of tributyltin hydride and 25 ml of anhydrous benzene for 3 days. The benzene is removed and the residue is concentrated further using short-path distillation (1 micron, 125° bath temperature). Crystallization of the residue from isopropyl alcohol gives 2.39 g of 2-cyclohexylmethyl-2,3,8,12b-tetrahydro-1H-3a,8-methanodibenzo[3,4:6,7]cyclohepta[1,2-c]pyrrol-1-one; nmr spectrum: τ 2.2–3.3 (m, 8); 5.9–6.2 (m, 2); 6.6–7.0 (m, 4); 8.1 (m, 2) and 8.1–9.7 (m, 11).

The above product is heated under reflux with 70 ml of 1 M diborane in tetrahydrofuran overnight. The excess diborane is destroyed with 15 ml of conc. hydrochloric acid; the mixture is concentrated, and the residue is heated under reflux with 15 ml of conc. hydrochloric acid and 20 ml of methanol for 3 days. After removal of the methanol the residue is made basic and extracted with methylene chloride. Removal of the solvent from the dried extracts gives 2.06 g of 2-cyclohexylmethyl-2,3,8,12b-tetrahydro-1H-3a,8-methanodibenzo[3,4:6,7]cyclohepta[1,2-c]pyrrole as an oil. An ether solution of the product is treated with hydrogen chloride, and the precipitate is crystallized from 90% ethanol to give 1.90 g of the hydrochloride, mp 218°–220° (dec).

Anal. Calcd for $C_{25}H_{30}ClN$: C, 79.02; H, 7.96; N, 3.69. Found: C, 78.62; H, 7.47; N, 3.66.

Further purification of the hydrochloride was achieved by drying it for several hours at about 110° and 0.2 micron pressure to give the product of Example 25, mp. 248°–253° (dec.).

EXAMPLE 46:

2-Cyclopropyl-2,3,8,12b-tetrahydro-1H-3a,8-methanodibenzo[3,4:6,7]cyclohepta[1,2-c]pyrrole; method II; nmr spectrum: τ 2.5–3.1 (m, 8); 6.0–8.4 (m, 9) and 9.4–9.8 (m, 4).

EXAMPLE 47:

2-Cyclobutyl-2,3,8,12b-tetrahydro-1H-3a,8-methanodibenzo[3,4:6,7]cyclohepta[1,2-c]pyrrole; method II; nmr spectrum: τ 2.7–3.2 (m, 8) and 6.1–8.5 (m, 15).

EXAMPLE 48:

2-Cyclopentyl-2,3,8,12b-tetrahydro-1H-3a,8-methanodibenzo[3,4:6,7]cyclohepta[1,2-c]pyrrole; method II; nmr spectrum: τ 2.6–3.2 (m, 8) and 6.1–8.8 (m, 17).

EXAMPLE 49:

2-Isopropyl-2,3,8,12b-tetrahydro-1H-3a,8-methanodibenzo[3,4:6,7]cyclohepta[1,2-c]pyrrole; method II; nmr spectrum: τ 2.7–3.2 (m, 8); 6.1–7.9 (m, 9); 8.8 (d, 6).

EXAMPLE 50:

2-(1-Cyclopentylethyl)-2,3,8,12b-tetrahydro-1H-3a,8-methanodibenzo[3,4:6,7]cyclohepta[1,2-c]pyrrole; method II; nmr spectrum: τ 2.7–3.1 (m, 8) and 6.1–9.1 (m, 21).

EXAMPLE 51:

2-(2-Methylcyclopentylmethyl)-2,3,8,12b-tetrahydro-1H-3a,8-methanodibenzo[3,4:6,7]cyclohepta[1,2-c]pyrrole; method II; nmr spectrum: τ 2.6–3.3 (m, 8) and 6.1–9.3 (m, 21). This compound is a mixture of two isomers in which the methyl group attached to the cyclopentane ring is cis and trans.

EXAMPLE 52:

2-(3-Methylcyclopentylmethyl)-2,3,8,12b-tetrahydro-1H-3a,8-methanodibenzo[3,4:6,7]cyclohepta[1,2-c]-pyrrole; method II; nmr spectrum: τ 2.6–3.3 (m, 8) and 6.0–9.5 (m, 21). This compound is a mixture of two isomers in which the methyl group attached to the cyclopentane ring is cis and trans.

EXAMPLE 53:

2-(2-Adamantylmethyl)-2,3,8,12b-tetrahydro-1H-3a,8-methanodibenzo[3,4:6,7]cyclohepta[1,2-c]pyrrole; method I; nmr spectrum: τ 2.6–3.0 (m, 8) and 6.0–8.5 (m, 25).

EXAMPLE 54:

2-(2-Thienylmethyl)-2,3,8,12b-tetrahydro-1H-3a,8-methanodibenzo[3,4:6,7]cyclohepta[1,2-c]pyrrole; method I; nmr spectrum: τ 2.7–3.3 (m, 11) and 5.9–8.0 (m, 10).

EXAMPLE 55:

2-(trans-2-Phenylcyclopropylmethyl)-2,3,8,12b-tetrahydro-1H-3a,8-methanodibenzo[3,4:6,7]cyclohepta[1,2-c]pyrrole; method I; nmr spectrum: τ 2.7–3.2 (m, 13) and 6.0–9.3 (m, 14).

EXAMPLE 56:

2-Tertiarybutyl-2,3,8,12b-tetrahydro-1H-3a,8-methanodibenzo[3,4:6,7]cyclohepta[1,2-c]pyrrole; method II; nmr spectrum: τ 2.6–3.0 (m, 8); 6.0–7.4 (m, 8); 8.7 (s, 9).

EXAMPLE 57:

Nitro-2-methyl-2,3,8,12b-tetrahydro-1H-3a,8-methanodibenzo[3,4:6,7]cyclohepta[1,2-c]pyrrole Hydrochloride To a solution of 1.5 g (5.06 mmoles) of 2-methyl-2,3,8,12b-tetrahydro-1H-3a,8-methanodibenzo[3,4:6,7]-cyclohepta[1,2-c]pyrrole hydrochloride in 25 ml of anhydrous hydrofluoric acid cooled at −78° was added 562 mg (5.06 mmoles) of potassium nitrate. The reaction mixture was allowed to warm to room temperature and the hydrofluoric acid was evaporated under a stream of nitrogen. The residue was dissolved in methylene chloride, and the solution washed with 1N aqueous sodium hydroxide, with water, and dried over potassium carbonate. The solvent was removed under vacuum, the residue was dissolved in ether and insolubles were removed by filtration. The ethereal filtrate was treated with dry hydrogen chloride to give 1.0 g of nitro-2-methyl-2,3,8,12b-tetrahydro-1H-3a,8-methanodibenzo[3,4:6,7]cyclohepta[1,2-c]pyrrole hydrochloride as a colorless solid, m.p. 202°–207° (slight decomp.).

Mass spectrum: Calcd. for $C_{19}H_{18}N_2O_2$: MW 306.174 Found: MW 306.137 Nmr spectrum of the free base: δ 2.2–4.2 (m, 11); 6.9–7.5 (m, 4); 7.8–8.3 (m, 3).

EXAMPLE 58

2-n-Propyl-2,3,8,12b-tetrahydro-1H-3a,8-methanodibenzo[3,4:6,7]cyclohepta[1,2-c]pyrrole; method II; nmr spectrum: τ 2.5–3.1 (m, 8); 6.0–7.7 (m, 10); 8.0–8.6 (m, 2) and 9.0 (t, 3).

EXAMPLE 59

2-n-Pentyl-2,3,8,12b-tetrahydro-1H-3a,8-methanodibenzo[3,4:6,7]cyclohepta[1,2-c]pyrrole; method II; nmr spectrum: τ 2.5–3.1 (m, 8); 6.0–7.7 (m, 10); and 8.0–9.3 (m, 9).

EXAMPLE 60

2-(3-Methylbutyl)-2,3,8,12b-tetrahydro-1H-3a,8-methanodibenzo[3,4:6,7]cyclohepta[1,2-c]pyrrole; method II; nmr spectrum: τ 2.6–3.2 (m, 8); 6.1–8.8 (m, 13) and 9.0 (d, 6).

EXAMPLE 61

2-(4-Phenylbutyl)-2,3,8,12b-tetrahydro-1H-3a,8-methanodibenzo[3,4:6,7]cyclohepta[1,2-c]pyrrole; method II; nmr spectrum: τ 2.6–3.1 (m, 13) and 6.0–8.5 (m, 16).

EXAMPLE 62

2-(2-Tetrahydrofurylmethyl)-2,3,8,12b-tetrahydro-1H-3a,8-methanodibenzo[3,4:6,7]cyclohepta[1,2-c]pyrrole; method II; nmr spectrum: τ 2.5–3.2 (m, 8) and 5.6–9.0 (m, 17).

EXAMPLE 63

5-Nitro-2-cyclopentylmethyl-2,3,8,12b-tetrahydro-1H-3a,8-methanodibenzo[3,4:6,7]cyclohepta[1,2-c]pyrrole Hydrochloride A solution of 10.0 g (27.4 mmoles) of 2-cyclopentylmethyl-2,3,8,12b-tetrahydro-1H-3a,8methanodibenzo[3,4:6,7]cyclohepta[1,2-c]pyrrole, the product of Example 7, and 6.6 g (65.3 mmoles) of potassium nitrate in 50 ml of trifluoroacetic acid was stirred overnight at room temperature and then poured onto ice-water. The product was extracted into methylene chloride and the organic layer was washed with water, with aqueous sodium hydroxide solution, with water and finally dried over potassium carbonate. The solution was evaporated to give 10.7 g of product. The 220MC nmr spectrum showed that only 5-nitro isomer was present.

In a second experiment, a solution of 15.0 g (41.0 mmoles) of the product of Example 7 and 4.56 g (45.1 mmoles) of potassum nitrate in liquid hydrogen fluoride was stirred overnight at room temperature under a stream of nitrogen. The solvent was evaporated, the residue was dissolved in methylene chloride, and the solution was treated as described above. The 220 MC nmr spectrum showed approximately 80% of the 5-nitro isomer. A sample of this product was purified by crystallization of the trifluoroacetic salt from ether-/ethyl acetate and then crystallization of the hydrochloride salt from acetone to give 5-nitro-2-cyclopentylmethyl-2,3,8,12b-tetrahydro-1H-3a,8-methanodibenzo[3,4:6,7]cyclohepta[1,2-c]pyrrole hydrochloride, mp 186–190°; infrared spectrum, 1420 cm$^{-1}$(NO$_2$). Analysis by high pressure liquid chromatography showed the presence of only one isomer.

Calcd. for $C_{24}H_{25}N_2O_2$: 374.1993 Mass measured: 374.2017 Nmr spectrum (60 MHz) of the free base: δ 1.0–4.0 (m, 19); 7.0–7.3 (m, 5); 8.0 (d of d, 1); 8.1 (d, 1).

EXAMPLE 64

5-Amino-2-cyclopentylmethyl-2,3,8,12b-tetrahydro-1H-3a, 8-methanodibenzo[3,4:6,7]cyclohepta[1,2-c]pyrrole Hydrochloride A solution of 5.0 g of 5-nitro-2-cyclopentylmethyl-2,3,8,12b-tetrahydro-1H-3a,8-methanodibenzo[2,4:6,7]-cyclohepta[1,2-c]pyrrole in tetrahydrofuran was hydrogenated at 25° with 0.3 g of platinum oxide at 50 lbs. hydrogen pressure to give 4.5 g of 5-amino-2-cyclopentylmethyl-2,3,8,12b-tetrahydro-1H-3a,8methanodibenzo[3,4:6,7]cyclohepta[1,2-c]pyrrole as an oil; nmr spectrum: δ 1.0–4.0 (m, 19); 3.4 (s, 2); 6.2–6.7 (m, 2); 6.8–7.2 (m, 5).

The hydrochloride salt was prepared in ether with dry hydrogen chloride, m.p. 344–347°. The salt was dried at 145°, 0.5 micron, for 8 hours, but it still retained a very small quantity of solvent.

Anal. Calcd. for $C_{24}H_{28}N_2$.HCl: C, 75.67; H, 7.62; N, 7.36 Found: C, 70.07; H, 7.55; N, 7.33.

EXAMPLE 65

5-Acetamido-2-cyclopentylmethyl-2,3,8,12b-tetrahydro1H-3a,8-methanodibenzo[3,4:6,7]cyclohepta[1,2-c]pyrrole Hydrochloride To a solution of 3.0 g (8.7 mmoles) of 5amino-2-cyclopentylmethyl-2,3,8,12b-tetrahydro-1H-3a, 8-methanodibenzo[3,4:6,7]cyclohepta[1,2-c]pyrrole and 10 ml of triethylamine in 25 ml of chloroform, cooled to 0°, was added dropwise 2.5 g (31.8 mmoles) of acetyl chloride. The reaction mixture was stirred overnight at room temperature and then for 30 minutes with 2.5 N aqueous sodium hydroxide. The organic layer was separated and the aqueous layer was extracted with methylene chloride. The combined organic extracts were washed with water, dried over potassium carbonate, and concentrated under vacuum. The residue was chromatographed on silica gel CC No. 7 with 57% methanol in chloroform to give 1.3 g of 5-acetamido-2-cyclopentylmethyl- 2,3,8,12b-tetrahydro1H-3a,8-methanodibenzo[3,4:6,7]cyclohepta[1,2-c]pyrrole as an oil; nmr spectrum: δ 1.0–4.0 (m, 19); 2.1 (s, 3); 6.8–7.8 (m, 7).

The hydrochloride salt was prepared in ether with dry hydrogen chloride, m.p. 199–208°.

Anal. Calcd. for $C_{26}H_{30}N_2$.HCl; C, 73.85; H, 7.34; N, 6.63; Cl, 8.4. Found: C, 71.19; H, 7.47; N, 6.37; Cl, 8.18.

EXAMPLE 66

5-Acetyl-2-cyclopentylmethyl-2,3,8,12b-tetrahydro-1H3a,8-methanodibenzo[3,4:6,7]cyclohepta[1,2-c]pyrrole Hydrochloride To a suspension of 5.0 g (37.39 mmoles) of aluminum chloride in 75 ml of methylene chloride, cooled to 0°, was added dropwise 3.0 g (38.2 mmoles) of acetyl chloride. Then 5.0 g (13.7 mmoles) of 2-cyclopentylmethyl-2,3,8,12b-tetrahydro1H-3a, 8-methanodibenzo[3,4:6,7]-cyclohepta[1,2-c]pyrrole was added portionwise. The reaction mixture was heated at reflux for several hours and then poured into 1N aqueous hydrochloric acid. The product was extracted with methylene chloride, and the extracts were washed with water, with 1N aqueous sodium hydroxide, with water and dried over potassium carbonate. The solvent was evaporated to leave 5.6 g of 5-acetyl-2-cyclopentylmethyl-2,3,8,12b-tetrahydro-1H-3a,8-methanodibenzo[3,4:6,7]cyclohepta[1,2-c]pyrrole as an oil; nmr spectrum: δ 1.0–4.0 (m, 19); 2.5 (s, 3); 7.1–7.25 (m, 5); 7.7–7.9 (m, 2). The 220MHz nmr spectrum showed that the product contained approximately 83% of the 5-acetyl isomer. A sample was purified by crystallization of the trifluoroacetate salt from ether/ethyl acetate and then of the hydrochloride salt from acetone, mp, 160–172° (dec.); ir. 1700 cm$^{-1}$ (COCH$_3$).

Anal. Calcd for C$_{26}$H$_{29}$NO.HCl: C, 76.56; H, 7.36; N, 3.43; Cl, 8.71 Found: C, 75.76; H, 7.45; N, 3.58; Cl, 8.22.

EXAMPLE 67

5-(α-Hydroxyethyl)-2-cyclopentylmethyl-2,3,8,12b-tetrahydro-1H-3a,8-methanodibenzo[3,4:6,7]cyclohepta[1,2-c]-pyrrole Hydrochloride To a suspension of 0.5 g of lithium aluminum hydride in 25 ml of ether was added dropwise a solution of 2.3 g of 5-acetyl-2-cyclopentylmethyl-2,3,8,12b-tetrahydro-1H-3a,8-methanodibenzo[3,4:6,7]cyclohepta[1,2-c]-pyrrole in 10 ml of ether. The reaction mixture was heated at reflux overnight and then excess lithium aluminum hydride was destroyed by the dropwise addition of a saturated aqueous sodium sulfate solution. The suspension was filtered with the aid of diatomaceous earth, and the filtrate was evaporated to dryness. The residue was dissolved in methylene chloride, and the solution was washed with water, dried over potassium carbonate and concentrated in vacuo to give 1.4 g of 5-(α-hydroxyethyl)-2-cyclopentylmethyl-2,3,8,12b-tetrahydro-1H-3a,8-methanodibenzo[3,4:6,7]cyclohepta[1,2-c]pyrrole as an oil; nmr spectrum; δ 1.0–4.0 (m, 19); 1.3 (d, 3); 3.0–4.0 (m, 1); 4.7 (t, 1); 6.8–7.4 (m, 7).

The hydrochloride salt was prepared in ether with dry hydrogen chloride, m.p. 156–165°.

Anal. Calcd. for C$_{26}$H$_{31}$NO.HCl: C, 76.19; H, 7.81; N, 3.42. Found: C, 74.97; H, 7.61; N, 3.27

EXAMPLE 68

5-Hydroxy-2-cyclopentylmethyl-2,3,8,12b-tetrahydro-1H-3a,8-methanodibenzo[3,4:6,7]cyclohepta[1,2-c]pyrrole Hydrochloride To a solution of 5.0 g (14.5 mmoles) of 5-amino-2-cyclopentylmethyl-2,3,8,12b-tetrahydro-1H-3a,8-methanodibenzo[3,4:6,7]cyclohepta[1,2-c]pyrrole, the product of Example 64, in 50 ml of 1N aqueous hydrochloric acid, cooled to 0°, was added dropwise a solution of 1.0 g (14.5 mmoles) of sodium nitrite in 5 ml of water. The reaction mixture was stirred overnight at room temperature, filtered and then heated to 90°. A precipitate of 5-hydroxy-2-cyclopentylmethyl-2,3,8,12b-tetrahydro-1H-3a,8-methanodibenzo[3,4:6,7]-cyclohepta[1,2-c]pyrrole hydrochloride was collected by filtration, m.p. 218–229°; nmr spectrum of free base: δ 1.0–4.0 (m, 19); 6.3–6.7 (m, 2); 6.7–7.2 (m, 5); 8.7 (s, 1). Anal. Calcd. for C$_{24}$H$_{27}$NO.HCl: C, 75.47; H, 7.34; N, 3.67; Cl, 9.3 Found: C, 71.75; H, 7.18 N, 3.68; Cl, 9.3.

EXAMPLE 69

5-Formyl-2-cyclopentylmethyl-2,3,8,12b-tetrahydro-1H-3a,8-methanodibenzo[3,4:6,7]cyclohepta[1,2-c]pyrrole Hydrochloride A solution of 5.0 g (13.6 mmoles) of 2-cyclopentylmethyl-2,3,8,12b-tetrahydro-1H-3a,8-methanodibenzo[3,4:6,7]cyclohepta[1,2-c]pyrrole in 100 ml of methylene chloride was cooled to 0° and 11.0 ml (19.0 g, 0.1 mole) of titanium tetrachloride was added dropwise over approximately 3.0 min. Then 6.0 g (52.2 mmoles) of α,α-dichloromethylether was added dropwise at 0°. The reaction mixture was allowed to warm to 25° and it was heated under reflux for one hour, cooled, and poured onto ice-water. The product was extracted into methylene chloride and the combined extracts were washed with water, with 10% aqueous sodium carbonate solution and then with water. The organic layer was dried and concentrated in vacuo to give 4.2 g of 5-formyl-2-cyclopentylmethyl-2,3,8,12b-tetrahydro-1H-3a,8-methanodibenzo[3,4:6,7]cyclohepta[1,2-c]pyrrole as an oil; nmr spectrum: δ 1.0–4.0 (m, 19); 6.9–7.3 (m, 5); 7.5 (d of d, b 1); 7.8 (d, 1); 9.86 (s, 1).

A sample was purified by crystallization of the trifluoroacetate salt from ether/ethyl acetate, crystallization of the hydrochloride salt from acetone and then recrystallization from acetonitrile, mp 170–5°, ir 1700 cm$^{-1}$ (CH=O).

EXAMPLE 70

5-Bromo-2-cyclopentylmethyl-2,3,8,12b-tetrahydro-1H-3a,8-methanodibenzo[3,4:6,7]cyclohepta[1,2-c]pyrrole Hydrochloride A solution of 5.0 g (14.55 mmoles) of 5-amino-2-cyclopentylmethyl-2,3,8,12b-tetrahydro-1H-3a,8-methanodibenzo[3,4:6,7]cyclohepta[1,2-c]pyrrole, (Example 64), in 25 ml of 40% hydrobromic acid, cooled at 5°, was diazotized with a solution of 1.1 g (16 mmoles) of sodium nitrite in 5 ml of water. The reaction mixture was allowed to warm to room temperature, filtered, and then added dropwise to a solution of 4.0 g (27.7 mmoles) of cuprous bromide in 25 ml of 48% hydrobromic acid. After standing overnight, dilution with water gave a precipitate which was collected by filtration. The solids were extracted with methylene chloride, and the organic layer washed with 1N aqueous sodium hydroxide solution was then with water. The extract was dried over potassium carbonate and evaporated to give 1.2 g of 5-bromo-2-cyclopentylmethyl-2,3,8,12b-tetrahydro-1H-3a,8-methanodibenzo[3,4:6,7]-cyclohepta[1,2-c]pyrrole as an oil; nmr spectrum δ 1.0–4.0 (m, 19); 6.8–7.5 (m, 7).

The hydrochloride salt was prepared in ether with dry hydrogen chloride.

Anal. Calcd. for: C$_{24}$H$_{26}$NBr.HCl: C, 64.80; H, 6.07; N, 3.15. Found: C, 62.78; H, 5.95; N, 3.47.

EXAMPLE 71

5-Acetyl-2-cyclopentylmethyl-2,3,8,12b-tetrahydro-1H-3a,8-methanodibenzo[3,4:6,7]cyclohepta[1,2-c]pyrrole Oxime Hydrochloride To a stirred mixture of 5.0 g (13.6 mmoles) of 5-acetyl-2-cyclopentylmethyl-2,3,8,12b-tetrahydro-1H-3a,8-methanodibenzo[3,4:6,7]cyclohepta[1,2-c]pyrrole, (Example 66), and 1.5 g (21.3 mmoles) of hydroxylamine hydrochloride in 25 ml of ethanol and 5.0 ml of water was added portionwise 2.8 g (70 mmoles) of powdered sodium hydroxide. The reaction mixture was then heated at reflux for 5 minutes, cooled, and distributed between water and methylene chloride. The organic layer was washed with water, dried over sodium sulfate and evaporated. The residue was chromatographed on silica gel CC No. 7 with 5% methanol in chloroform to give 1.3 g of 5-acetyl-2-cyclopentylmethyl-2,3,8,12b-tetrahydro-1H-3a,8-methanodibenzo[3,4:6,7]cyclohepta[1,2-c]pyrrole oxime as an oil; nmr spectrum: δ 1.0–4.0 (m, 19); 2.2 (s, 2); 6.8–7.4 (m, 7); 7.5 (s, 1).

The hydrochloride salt was prepared in ether with dry hydrogen chloride.

Anal. Calcd. for $C_{26}H_{30}N_2O \cdot HCl$: C, 73.85; H, 7.34; N, 6.63. Found: C, 73.56; H, 7.37; N, 6.37.

Example 72

5,11-Diamino-2-cyclopentylmethyl-2,3,8,12b-tetrahydro-1H-3a,8-methanodibenzo[3,4:6,7]cyclohepta[1,2-c]pyrrole A solution of 5.0 g of 5,11-dinitro-2-cyclopentylmethyl-2,3,8,12b-tetrahydro-1H-3a,8-methanodibenzo[3,4:6,7]cyclohepta[1,2-c]pyrrole in tetrahydrofuran was hydrogenated at 50 lbs. pressure and room temperature with 0.2 g of platinum oxide catalyst to give 5.3 g of 5,11 -diamino-2-cyclopentylmethyl-2,3,8,12b-tetrahydro-1H-3a,8-methanodibenzo[3,4:6,7]cyclohepta[1,2-c]pyrrole as an oil; nmr spectrum: δ 1.0–4.0 (m, 19); 3.4 (s, 4); 6.2–6.7 (m, 4); 6.8–7.0 (m, 2).

A hydrochloride salt was prepared in either with dry hydrogen chloride.

The 5,11-dinitro compound used as starting materal was prepared by the following procedure. 2-Cyclopentylmethyl-2,3,8,12b-tetrahydro-1H-3a,8-methanodibenzo[3,4:6,7]cyclohepta[1,2-c]pyrrole (10.0 g, 27.36 mmoles) was nitrated with 5.6 g (55.4 mmoles) of potassium nitrate in liquid hydrogen fluoride to give 5.5 g of 5,11-dinitro-2-cyclopentylmethyl-2,3,8,12 b-tetrahydro-1H-3a,8-methanodibenzo[3,4:6,7]cyclohepta[1,2-c]pyrrole. The hydrochloride salt was prepared in acetonitrile, separated, and recrystallized from nitromethane to give 3.3 g of purified product, mp. 205–214° (dec.); ir spectrum: 1340 cm$^{-1}$ (NO$_2$). High pressure liquid chromatography showed the presence of only one isomer.

Calcd for $C_{24}H_{25}N_3O_4 \cdot HCl$: 419.1844. was measured: 419.1874. Anal. Calcd for $C_{24}H_{25}N_3O_4 \cdot HCl$: C, 63.22; H, 5.71; N, 9.22; Cl, 7.79 Found: C, 60.37; H, 5.54; N, 8.8; Cl, 7.03.

EXAMPLE 73

2-Cyclopentylmethyl-2,3,8,12b-tetrahydro-1H-3a,8-methanodibenzo[3,4:6,7]cyclohepta[1,2-c]pyrrole-5-carboxylic Acid Hydrochloride A solution of 6.5 g (38.2 mmoles) of silver nitrate in 50 ml of 50% aqueous ethanol was added to a solution of 4.0 g (0.1 mmole) of NaOH in 50 ml of 50% aqueous ethanol and this mixture was added to a mixture of 4.2 g (11.8 mmoles) of 5-formyl-2-cyclopentylmethyl-2,3,8,12b-tetrahydro-1H-3a,8-methanodibenzo[3,4:6,7]-cyclohepta[1,2-c]pyrrole (Example 69) in 25 ml of ethanol. The reaction mixture was heated at reflux overnight and then filtered. The filtrate was acidified with conc. hydrochloric acid, diluted with water and extracted with methylene chloride. The combined extracts were evaporated and the residual oil crystallized from acetone to give 1.2 g of 2-cyclopentylmethyl-2,3,8,12b-tetrahydro-1H-3a,8-methanodibenzo[3,4:6,7]-cyclohepta[1,2-c]pyrrole-5-carboxylic acid hydrochloride, mp, 340°–5° (dec.). ir 1720 cm$^{-1}$ (CO$_2$H); nmr spectrum: δ 1.0–1.9 (m, 9); 2.2–2.6 (m, 2); 3.0–3.8 (m, 4); 3.9–4.5 (m, 4); 6.8–7.5 (m, 5); 7.5–8.2 (m, 2).

Anal. Calcd for $C_{25}H_{27}NO_2 \cdot HCl$: C, 73.26; H, 6.84; N, 3.42; Cl, 8.67 Found: C, 72.09; H, 6.60; N, 3.59; Cl, 8.4

EXAMPLE 74

2-Cyclopentylmethyl-2,3,8,12b-tetrahydro-1H-3a,8-methanodibenzo[3,4:6,7]cyclohepta[1,2-c]pyrrole-5-carboxylic Acid Hydrochloride, Methyl Ester The methyl ester of the carboxylic acid of Example 73 was prepared by reaction of the carboxylic acid with methanol and thionyl chloride and converted to the hydrochloride salt, mp 160° (dec.): ir 1750 cm$^{-1}$ (CO$_2$CH$_3$); nmr spectrum of free base: δ: 1.0–4.0 (m, 22); 6.9–7.3 (m, 5); 7.7 (d of d, 1); 8.0 (d, 1).

EXAMPLE 75

5-[1-(1-Hydroxy-3-butenyl)]-2-cyclopentylmethyl-2,3,8,12b-tetrahydro-1H-3a,8-methanodibenzo[3,4:6,7]-cyclohepta[1,2-c]pyrrole Hydrochloride A solution of 3.0 g (8.4 mmoles) of 5-formyl-2-cyclopentylmethyl-2,3,8,12b-tetrahydro-1H-3a,8-methanodibenzo[3,4:6,7]cyclohepta[1,2-c]pyrrole (Example 69) in 25 ml of ether was added dropwise to the Grignard reagent prepared from 4.0 g (33.6 mmoles) of allyl bromide and 0.8 g (33.3 mmoles) of magnesium in 25 ml of ether. The reaction mixture was stirred at room temperature overnight and then poured onto a saturated aqueous ammonium chloride solution. The product was extracted into methylene chloride, and the organic layer was washed with 1N aqueous sodium hydroxide solution and with water. The methylene chloride solution was dried over potassium carbonate and evaporated to give 5-[1-(1-hydroxy-3-butenyl)]-2-cyclopentylmethyl-2,3,8,12b-tetrahydro-1H-3a,8-methanodibenzo[3,4:6,7]cyclohepta[1,2-c]pyrrole as an oil; nmr spectrum: δ 1.0–4.0 (m, 19); 2.2–3.9 (m, 4); 4.9–5.2 (m, 2); 5.3–5.8 (m, 1); 6.8–7.5 (m, 7). The hydrochloride salt was prepared in ether with dry hydrogen chloride, m.p. 162° (dec.).

EXAMPLE 76

5-Chloro-2-cyclopentylmethyl-2,3,8,12b-tetrahydro-1H-3a,8-methanodibezno[3,4:6,7]cyclohepta[1,2-c]pyrrole Hydrochloride A solution of 2.5 g (6.02 mmoles) of 5-amino-2-cyclopentylmethyl-2,3,8,12b-tetrahydro-1H-3a,8-methanodibenzo[3,4:6,7]cyclohepta[1,2-c]pyrrole (Example 64) in 25 ml of 80% hydrochloric acid, cooled to 0°, was diazotized with a solution of 0.5 g (7.23 mmoles) of sodium nitrite in 2.5 ml of water. The reaction mixture was added dropwise to a solution of 1.3 g (13.14 mmoles) of cuprous chloride in 25 ml of 80% hydrochloric acid. The reaction mixture was allowed to stand overnight and then distributed between water and methylene chloride. The organic layer was washed with water, 1N aqueous sodium hydroxide solution, and then with water, dried over sodium sulfate, and evaporated to give 2.0 g of 5-chloro-2-cyclopentylmethyl-2,3,8,12b-tetrahydro1H-3a,8-methanodibenzocyclohepta[1,2-c]pyrrole as an oil.

A sample was purified by crystallization of the trifluoroacetate salt from ether and then of the hydrochloride salt from acetone; nmr spectrum of the free base: δ 1.0–4.0 (m, 19); 7.0–7.25 (m, 7).

EXAMPLE 77

5-Fluoro-2-cyclopentylmethyl-2,3,8,12b-tetrahydro-1H-3a,8-methanodibenzo[3,4:6,7]cyclohepta[1,2-c]pyrrole Hydrochloride A solution of 5.0 g (14.5 mmoles) of 5-amino-2-cyclopentylmethyl-2,3,8,12b-tetrahydro-1H,3a,8-methanodibenzo[3,4:6,7]cyclohepta[1,2-c]-pyrrole (Example 64) in 60 ml of 6N aqueous hydrochloric acid, cooled to 0°, was diazotized with a solution of 1.1 g (16.9 mmoles) of sodium nitrite in 4.1 ml of water. At 0° the reaction mixture was saturated with sodium fluoroborate and extracted with ethyl acetate. Evaporation of the solvent under vacuum gave 5.0 g of the diazonium fluoroborate salt, which was thermally decomposed. The residue was distributed between water and methylene chloride and the organic layer was washed with 1N aqueous sodium hydroxide solution and then with water. The methylene chloride solution was dried over potassium carbonate and evaporated to afford 2.1 g of 5-fluoro-2-cyclopentylmethyl-2,3,8,12b-tetrahydro-1H-3a,8-methanodibenzo[3,4:6,7]-cyclohepta[1,2-c]pyrrole; nmr spectrum: $\delta$ 1.0–4.0 (m, 19); 6.6–7.4 (m, 7); $F^{19}$ nmr (fluorotrichloromethane reference) decoupled showed a singlet at 116.3 ppm. The hydrochloride salt was prepared in ether with dry hydrogen chloride.

EXAMPLE 78

5-Difluoromethyl-2-cyclopentylmethyl-2,3,8,12b-tetrahydro-1H-3a,8-methanodibenzo[3,4:6,7]cyclohepta[1,2c]pyrrole Hydrochloride A solution of 3.0 g (7.6 mmoles) of 5-formyl-2-cyclopentylmethyl-2,3,8,12b-tetrahydro-1H-3a,8-methanodibenzo[3,4:6,7]cyclohepta[1,2-c]pyrrole hydrochloride (Example 69) in 25 ml of methylene chloride was cooled to 0° and treated with 3.0 ml (23.8 mmoles) of diethylaminosulfur trifluoride (Middleton, U.S. Pat. No. 3,914,265). The reaction mixture was stirred at room temperature overnight and then poured onto ice-water. The product was extracted into methylene chloride and the organic layer was washed with water, with aqueous sodium hydroxide solution and again with water. The extract was dried over potassium carbonate and evaporated to afford 3.0 g of 5-difluoromethyl-2-cyclopentylmethyl-2,3,8,12b-tetrahydro-1H-3a,8-methanodibenzo [3,4:6,7]cyclohepta[1,2-c]pyrrole. A sample was purified by crystallization of the trifluoroacetate salt from ether and then of the hydrochloride salt from acetone, mp 240°–251° (dec.); nmr spectrum of the free base: $\delta$ 1.0–4.0 (m, 19); 6.6 (t, 1); 7.0–7.1 (m, 6); 7.4 (d, 1); $F^{19}$ nmr (fluorotrichloromethane reference) of the free base showed a triplet centered at 109.72 ppm (decoupled a doublet 109.38 ppm and 110.10 ppm).

EXAMPLE 79

5,11-Dichloro-2-cyclopentylmethyl-2,3,8,12b-tetrahydro1H-3a,8-methanodibenzo[3,4:6,7]cyclohepta[1,2-c]pyrrole Hydrochloride A solution of 4.8 g (13.3 mmoles) of 5,11-diamino-2-cyclopentylmethyl-2,3,8,12b-tetrahydro-1H-3a,8-methanodibenzo[3,4:6,7]cyclohepta[1,2-c]pyrrole (Example 72) in 50 ml of 80% hydrochloric acid, cooled at 0°, was diazotized with a solution of 1.0 g (14.5 mmoles) of sodium nitrite in 5 ml of water. The reaction mixture was added dropwise to a solution of 2.6 g (26.3 mmoles) of cuprous chloride in 40 ml of concentrated hydrochloric acid. The reaction mixture was allowed to stand overnight and then distributed between water and methylene chloride. The organic layer was washed with water, with 1N aqueous sodium hydroxide solution and then with water. The methylene chloride solution was dried over potassium carbonate and evaporated. The residual oil was chromatographed on silica gel CC #7 with chloroform to give 1.4 g of 5,11-dichloro-2-cyclopentylmethyl-2,3,8,12b-tetrahydro1H,3a,8-methanodibenzo[3,4:6,7]cyclohepta[1,2-c]pyrrole as an oil; nmr spectrum: $\delta$ 1.0–4.0 (m, 19); 7.0–7.2 (m, 6). The hydrochloride salt was prepared in ether with dry hydrogen chloride. A sample was purified by crystallization of the trifluoroacetate salt from ether.

EXAMPLE 80

11-Chloro-2-methyl-2,3,8,12b-tetrahydro-1H-3a,8-methanodibenzo[3,4:6,7]cyclohepta[1,2-c]pyrrole Hydrochloride A solution of 4.0 g of 8-chloro-2-methyl1,2,3,5-tetrahydro-5,9b-o-benzenobenz[e]isoindole, prepared as described below, in 15 ml of trifluoroacetic acid was heated at 175° C for 12 hours in Carius tube. Trifluoroacetic acid was removed in vacuo and a solution of the residue in methylene chloride was added dropwise to a cooled, stirred mixture of 200 m of 2N sodium hydroxide and methylene chloride. The organic layer was separated, washed with water, dried and evaporated to give 2.2 g of 11-chloro-2-methyl-2,3-dihydro-8H-3a,8-methanodibenzo[3,4:6,7]cyclohepta[1,2-c]pyrrole as an oil; nmr spectrum: $\delta$ 2.1 and 2.6 (ABQ, J = 9 Hz; the lower field component is split again by 4 Hz; the higher field component by ca 1 Hz; 2); 2.7 (s, 3); 3.2 and 3.9 (ABQ, J = 10 Hz, 2); 3.9 (d, 4 Hz, 1); 6.1 (s, 1); 6.7–7.5 (m, 7).

A solution of the oil (7.5 mmoles) in 25 ml of tetrahydrofuran was treated with dry hydrogen chloride with cooling until just acid. A solution of 1.4 g (22.3 mmoles) of sodium cyanoborohydride in 20 ml of methanol was immediately added. The reaction mixture was stirred for several hours at room temperature and then concentrated in vacuum. The residue was distributed between 1N sodium hydroxide and methylene chloride. The organic layer was separated, washed with water, dried and evaporated to give 11-chloro-2-methyl2,3,8,12b-tetrahydro-1H,3a,8-methanodibenzo[3,4:6,7]cyclohepta[1,2-c]pyrrole as an oil. The hydrochloride salt was prepared in ether; mp 185°–195° (dec.). The nmr spectrum of the free base: $\delta$ 2.2–4.1 (n, 11); 6.8–7.4 (m, 7); the former area at 220 MHz showed 2 isomers, approximately 8:1, presumably the 11-chloro and 5-chloro, arising as a consequence of the Wagner-Meerwein rearrangement; and resolved from low to high field, into a doublet (J = 4.5 Hz; 1); a doublet (J = 10 Hz, 1); a doublet of doublets (J = 7 and 8 Hz, 1); a doublet of doublets (J = 8 and 10 Hz, 1); a 2 proton multiplet; a 3 proton singlet; and an ABX pattern ($J_{AB}$ = 10.5 Hz, $J_{AX}$ = 4.5 Hz, $J_{BX} \simeq$ 0, 2).

Anal. Calcd. for $C_{19}H_{18}ClN.HCl$: C, 68.27; H, 5.72; N, 4.22 Found: C, 66.72; H, 5.24; N, 3.84.

Molecular weight: Calc. for $C_{19}H_{18}ClN$: 295.1128 Measured (mass spectrum): 295.1088

8-Chloro-2-methyl-1,2,3,5-tetrahydro-5,9b-o-benzobenz[e]isoindole was prepared as follows. A suspension of 30.0 g (0.12 mole) of 2-chloroanthraldehyde in 300 ml of ethanol was heated at reflux with 45 ml (31.5 g; 1.0 mole) of methylamine for 30 minutes. Insolubles were removed by filtration of the hot reaction mixture. The cooled filtrate crystallized to yield 11.8 g of 2 chloroanthraldehyde methylimine, mp 136°-8°; nmr spectrum δ 3.8 (d, 3); 7.2-8.6 (m, 8); 9.3 (s, 1).

To a slurry of 11.8 g (46.5 mmoles) of the imine in 80 ml of methanol and 12.5 ml of acetic acid was added portionwise 7.0 g (0.11 mole) of sodium cyanoborohydride with cooling. The reaction mixture was stirred overnight at room temperature and then acidified with 31 ml of concentrated hydrochloric acid with cooling. After stirring for 30 minutes at room temperature the reaction mixture was made basic with 6N sodium hydroxide and then distributed between water and methylene chloride. Some insoluble material was removed by filtration and the organic layer was separated, dried and evaporated to give 10.1 g of 2-chloro-N-methyl-9-anthracenemethylamine as an amber oil; nmr spectrum: δ 1.6 (s, 1); 2.5 (s, 3); 4.4 (s, 2); 7.1-8.3 (m, 8).

A mixture of 13.1 g (51.3 mmoles) of the amine, 30.0 g (0.22 mole) of propargyl bromide and 43.0 g (0.33 mole) of diisopropylethylamine in 75 ml of tetrahydrofuran was stirred at room temperature for two days. The reaction mixture was concentrated in vacuum and the residue distributed between water and methylene chloride. The organic layer was washed with water, dried and evaporated to give 12.1 g of 2-chloro-N-methyl-N-propargylanthracene-9-methylamine as an oil which was mixed with some cyclized product (see below). The nmr spectrum of the product showed characteristic peaks at: δ 2.35 (s, NCH$_3$); 3.2 (d, NCH$_2$C≡CH); 4.33 (s, ArCH$_2$); 7.1-8.6 (m, Ar).

A solution of the propargylamine in 100 ml of xylene was heated at reflux overnight. The solvent was removed under reduced pressure and the residue chromatographed on silica gel CC No. 7 using chloroform to give 4.0 g of 8-chloro-2-methyl-1,2,3,5-tetrahydro-5,9b-o-benzenobenz[e]isoindole as a light yellow oil; nmr spectrum: δ 2.5 (s, 3); 3.2 (d, 2 Hz, 2); 3.6 (s, 2); 5.0 (d, 6 Hz, 1); 6.5 (d/t, 6/2 Hz, 1); 6.8-7.3 (m, Ar).

EXAMPLE 81

11-Chloro-2-cyclohexylmethyl-2,3,8,12b-tetrahydro-1H-3a,8-methanodibenzo[3,4:6,7]cyclohepta[1,2-c]-pyrrole Hydrochloride 8-Chloro-2-cyclohexylmethyl-1,2,3,5-tetrahydro-5,9b-o-benzenobenz[e]isoindole, prepared as described below, was rearranged with trifluoroacetic acid (as described in Example 80 for the N-methyl compound) to give 11-chloro-2-cyclohexylmethyl-2,3-dihydro-8H-3a,8-methanodibenzo[3,4:6,7]cyclohepta[1,2-c]pyrrole as an oil; nmr spectrum: δ 0.7-2.1 (m, 11); 2.1 and 2.6 (ABQ, J = 9 Hz; the lower field component is split again by 4 Hz; 2); 2.8 (t, 2); 3.2 (d, 10 Hz, 1); 3.9 (m, 2); 6.1 (s, 1); 6.7-7.5 (m, 7).

Reduction of this intermediate with sodium cyanoborohydride gave 11-chloro-2-cyclohexylmethyl-2,3,8,12b-tetrahydro-1H-3a,8-methanodibenzo[3,4:6,7]-cyclohepta[1,2-c]pyrrole, isolated from 2-propanol as the hydrochloride salt, mp. 239°-242° dec; nmr spectrum of the free base: δ 0.5-4.0 (m, 21), 6.9-7.5 (m, 7); the former area at 220 Mz showed 2 isomers, approximately 3:1; presumably the 11-chloro and 5-chloro compounds arising as a consequence of the Wagner-Meerwein rearrangement; and resolved from low to high field, into a doublet (J = 4 Hz, 1); a doublet (J = 10 Hz, 1); a doublet of doublets (J = 7 and 8 Hz, 1); a doublet of doublets (J = 7 and 10 Hz, 1); a 4 proton multiplet; and an ABX pattern (J$_{AB}$ = 11 Hz, J$_{AX}$ = 4.0 Hz, J$_{BX}$ ~ 0, 2).

Anal. Calcd. for C$_{25}$H$_{28}$ClN.HCl: C, 72.46; H, 7.0; N, 3.8 Found: C, 69.88; H, 6.89; N, 3.25.

Molecular weight: Calc. for C$_{25}$H$_{28}$ClN: 295.1128 Measured (mass spectrum): 295.1088

8-Chloro-2-cyclohexylmethyl-1,2,3,5-tetrahydro-5,9b-o-benzenobenz[e]isoindole was prepared from 2-chloroanthraldehyde and cyclohexylmethylamine by the procedure described for the analogous 2-methyl compound (Example 80). The intermediates have the following physical properties:

2-Chloroanthraldehyde N-cyclohexylmethylimine mp. 106°-7°, (ethanol); nmr spectrum: δ 1.02-2.1 (m, 11); 3.7 (d, 2); 7.1-8.5 (m, 8); 9.0 (s, 1).

Anal. Calcd. for C$_{22}$H$_{22}$ClN: C, 78.69; H, 6.56; N, 4.17 Found: C, 78.43; H, 6.28; N, 4.20.

2-Chloro-N-cyclohexylmethyl-9-anthracenemethylamine (oil); nmr spectrum: δ 1.0-2.1 (m, 12); 2.7 (d, 2); 4.5 (s, 2); 7.1-8.3 (m, 8).

2-Chloro-N-cyclohexylmethyl-N-propargyl-9-anthracenemethylamine (oil); nmr spectrum: δ 1.0-2.0 (m, CH$_2$); 2.4 (d, NCH$_2$); 3.2 (d, NCH$_2$C≡CH); 4.4 (s, ArCH$_2$); 6.7-8.2 (m, Ar).

8-Chloro-2-cyclohexylmethyl-1,2,3,5-tetrahydro-5,9b-o-benzenobenzo[e]isoindole (hydrochloride salt from 2-propanol), mp 135°-137°; nmr spectrum of the free base: δ 1.0—2.1 (m, 11); 2.4 (d, 2); 3.2 (d, 2Hz, 2); 3.6 (s, 2); 5.0 (d, 6 Hz, 1); 6.4 (d/t, 6/2 Hz, 1); 6.7-7.3 (m, Ar).

Anal. Calcd. for C$_{25}$H$_{26}$ClN: C, 79.89; H, 6.9; N, 3.7 Found: C, 79.33; H, 7.14; N, 3.77.

EXAMPLE 82

5-Azido-2-cyclopentylmethyl-2,3,8,12b-tetrahydro-1H-3a,8-methanodibenzo[3,4:6,7]cyclohepta[1,2-c]-pyrrole To a solution of 6.5 g (0.019 mole) of 5-amino-2-cyclopentylmethyl-2,3,8,12b-tetrahydro-1H-3a,8-methanodibenzo[3,4:6,7]cyclohepta[1,2-c]pyrrole (Example 64) in 5ml of conc. hydrochloric acid and 120 ml of water, cooled to 0°, was added an ice cold solution of 1.5 g (.022 mole) of sodium nitrite in 5 ml of water over a 5 minute period. After stirring 10 minutes at 0°, an ice cold solution of 1.4 g (.022 mole) of sodium azide in 5 ml of water was added portionwise. A cream-colored precipitate formed followed by copious evolution of nitrogen. Stirring was continued for 1 hour at 0°. The reaction mixture was made basic (pH 13) with sodium hydroxide and allowed to stand overnight. It was dissolved in methylene chloride, the organic layer was separated, washed with water and dried over potassium carbonate. Evaporation of the solvent gave 4 g of the crude azide as a deep red oil. It was purified by chromatography on silica gel (5% methanol-chloroform) to give 5-azido-2-cyclopentylmethyl-2,3,8,12b-tetrahydro-1H-3a,8-methanodibenzo[3,4:6,7]cyclohepta[1,2-c]pyrrole; ir spectrum: strong —N═N═N absorption at 2100 cm$^{-1}$.

Molecular weight: Calcd. for C$_{24}$H$_{26}$N$_4$: 370.2156 Found (mass spectrum): 370.2155

EXAMPLE 83

5-Formyl-2-cyclopentylmethyl-2,3,8,12b-tetrahydro-1H-3a,8-methanodibenzo[3,4:6,7]cyclohepta[1,2-c]pyrrole Oxime Hydrochloride To a suspension of 6.6 g (0.02 mole) of 5-formyl-2-cyclopentylmethyl-2,3,8,12b-tetrahydro-1H-3a,8-methanodibenzo[3,4:6,7]cyclohepta[1,2-c]pyrrole (Example 69) and 2.0 g (0.03 mole) of hydroxylamine hydrochloride in 25 ml of ethanol was added dropwise a solution of 1.6 g (.04 mole) of sodium hydroxide in 5 ml of water. The reaction mixture was stirred for 30 minutes and heated under reflux for 5 minutes. A yellow solid precipitated. The reaction mixture was diluted with water, extracted with methylene chloride, and the extract was dried over potassium carbonate and concentrated. The resulting oil was dissolved in ether and filtered. Evaporation of the ether gave the product, 5-formyl-2-cyclopentylmethyl-2,3,8,12b-tetrahydro-1H-3a,8-methanodibenzo[3,4:6,7]cyclohepta[1,2-c]pyrrole oxime, as an oil which was crystallized by the addition of pet. ether. The oxime was dissolved in ether and the solution was acidified to give 3.8 g of the hydrochloride salt; mp. 200°–205° (with dec. starting at 185°).

Calcd. for $C_{25}H_{28}N_2O$: C, 80.61; H, 7.58; N, 7.52 Found: C, 79.67; H, 7.35; N, 6.78. MW Calcd: 372.2202 Found (mass spectrum): 372.2216

EXAMPLE 84

5-Formyl-2-cyclopentylmethyl-2,3,8,12b-tetrahydro-1H-3a,8-methanodibenzo[3,4:6,7]cyclohepta[1,2-c]pyrrole Oxime-O-(N-methylcarbamate) Hydrochloride Two g (.005 mole) of 5-formyl-2-cyclopentylmethyl-2,3,8,12b-tetrahydro-1H-3a,8-methanodibenzo[3,4:6,7]-cyclohepta[1,2-c]pyrrole oxime (Example 83) was dissolved in 20 ml of benzene containing two drops of dibutyltin dilaurate and cooled to 10°–15°. To this solution was added dropwise a solution of 0.7 g (.008 mole) of methyl isocyanate in 10 ml of benzene. The reaction mixture was stirred at room temperature for one hour, concentrated, and the resulting oil was solidified by the addition of pet. ether to give 1.4 g of crude 5-formyl-2-cyclopentylmethyl-2,3,8,12b-tetrahydro-1H-3a,8-methanodibenzo[3,4:6,7]cyclohepta[1,2-c]pyrrole oxime-O-(N-methylcarbamate). The product was chromatographed on silica gel using 5% methanol-chloroform to give 0.9 g of purified product which was converted to the hydrochloride salt. The infrared spectrum of the salt showed strong —NH absorption at 3300 $cm^{-1}$ and —C═O absorption at 1725 $cm^{-1}$.

EXAMPLE 85

5-Cyano-2-cyclopentylmethyl-2,3,8,12b-tetrahydro-1H-3a,8-methanodibenzo[3,4:6,7]cyclohepta[1,2-c]-pyrrole Hydrochloride A solution of 20 g of 5-formyl-2-cyclopentylmethyl-2,3,8,12b-tetrahydro-1H-3a,8-methanodibenzo[3,4:6,7]-cyclohepta[1,2-c]pyrrole oxime (Example 83) in 175 ml of acetic anhydride was heated at reflux for one hour and stirred overnight. The acetic anhydride was removed under vacuum and the resulting oil was dissolved in methylene chloride, the solution was washed with 0.1 N sodium hydroxide solution, with water, and finally with saturated satl solution. It was dried and the solvent evaporated to give 15.8 g of crude nitrile. The product was chromatographed on florisil using chloroform followed by 5% methanol-chloroform to give 6 g of purified 5-cyano-2-cyclopentylmethyl-2,3,8,12b-tetrahydro-1H-3a,8-methanodibenzo[3,4:6,7]cyclohepta[1,2-c]pyrrole. The free base was dissolved in ether, converted to the hydrochloride salt, and the salt was recrystallized from ethyl acetate-methanol; white solid, mp 165° (dec.), 168°–170°. The infrared sepctrum had strong CN absorption at 2200 $cm^{-1}$.

MW calc. for $C_{25}H_{26}N_2$: 354.2096 Found (mass spectrum): 354.2090

EXAMPLE 86

2-Cyclopentylmethyl-2,3,8,12b-tetrahydro-1H-3a,8-methanodibenzo[3,4:6,7]cyclohepta[1,2-c]pyrrole-5-methanol Hydrochloride Five g of 5-formyl-2-cyclopentylmethyl-2,3,8,12b-tetrahydro-1H-3a,8-methanodibenzo[3,4:6,7]cyclohepta[1,2-c]pyrrole (Example 69) in 100 ml of ethanol and 0.1g of $PtO_2$ catalyst was hydrogenated at 25° under 3 atm. of hydrogen pressure for two hours. The mixture was filtered through diatomaceous earth, and the solvent was evaporated. The resulting oil was dissolved in ether and the solution acidified with gaseous hydrogen chloride. A total of 1.9 g of 2-cyclopentylmethyl-2,3,8,12b-tetrahydro-1H-3a,8-methanodibenzo[3,4:6,7]-cyclohepta[1,2-c]pyrrole-5 -methanol hydrochloride was isolated, mp 290–293°. The infrared spectrum showed characteristic OH absorption at 3300 $cm^{-1}$.

Anal. Calcd for $C_{25}H_{29}NO \cdot HCl$: C, 75.83; H, 7.64; N, 3.54 Found: C, 75.33; H, 7.67; N, 3.63.

EXAMPLE 87

5-Fluoromethyl-2-cyclopentylmethyl-2,3,8,12b-tetrahydro-1H-3a,8-methanodibenzo[3,4:6,7]cyclohepta[1,2-c]-pyrrole Hydrochloride 1.0 g of 2-cyclopentylmethyl-2,3,8,12b-tetrahydro-1H-3a,8-methanodibenzo[3,4:6,7]cyclohepta[1,2-c]-pyrrole-5-methanol hydrochloride was dissolved in 25 ml of methylene chloride and the solution was cooled to 0°. To this solution was added dropwise a solution of 1.0 g of diethylaminosulfur trifluoride (Middleton, U.S. Pat. 3,914,265) in 10 ml of methylene chloride. After the addition was completed, the solution was stirred at 25° overnight, poured over ice, separated and the organic layer was washed with 0.1 N sodium hydroxide, with water, with saturated salt solution and dried over potassium carbonate. Evaporation of the solvent left 1.3 g of 5-fluoromethyl-2-cyclopentylmethyl-2,3,8,12b-tetrahydro-1H-3a,8-methanodibenzo[3,4:6,7]cyclohepta[1,2-c]pyrrole. It was dissolved in acetone and the solution was acidified with gaseous hydrogen chloride. The hydrochloride salt was recrystallized from ethyl acetate-methanol.

The presence of fluorine was confirmed by $^{19}F$ nmr.

Calcd. for $C_{25}H_{28}NF$: MW = 361.2169 Found (mass spectrum): 361.2204

EXAMPLE 88

2-Cyclopentylmethyl-2,3,8,12b-tetrahydro-1H-3a,8-methanodibenzo[3,4:6,7]cyclohepta[1,2-c]pyrrole-5-N-methylsulfonamide Hydrochloride Three g (.007 mole) of 2-cyclopentylmethyl-2,3,8,12b-tetrahydro-1H-3a,8-methanodibenzo[3,4:6,7]-cyclohepta[1,2-c]pyrrole-5-sulfonyl chloride, prepared as described below, was suspended in 75 ml of acetone, and the suspension was added portionwise to 75 ml of 40% aqueous methylamine. The resulting blue solution was heated to 50° on a steam bath during which time the color changed to yellow-brown. Removal of the solvent left a brown oil which was dissolved in methylene chloride. The organic layer was washed with water, dried, and the solvent evaporated to leave 3.3 g of crude 2-cyclopentylmethyl-2,3,8,12b-tetrahydro-1H-3a,8-methanodibenzo[3,4:6,7]cyclohepta[1,2-c]pyrrole-5-N-methylsulfonamide. It was chromatographed on silica gel using 5% methanol-chloroform to give 2.3 g of the purified product. The product was converted to the hydrochloride salt, and it was recrystallized from acetone. The infrared spectrum has strong —$SO_2$— absorption in the 1140 and 1300 cm$^{-1}$ region and NH-absorption at 3250 cm$^{-1}$.

MW calcd. for $C_{25}H_{30}N_2O_2S$: 422.2026 Found (mass spectrum): 422.2039

The sulfonyl chloride starting material was prepared by the following procedure. A solution of 6.0 g of 5-amino-2-cyclopentylmethyl-2,3,8,12b-tetrahydro-1H-3a,8-methanodibenzo[3,4:6,7]cyclohepta[1,2-c]pyrrole (Example 64) in 12 ml of concentrated hydrochloric acid and 34 ml of water was cooled to 0°. To this solution was added dropwise a saturated solution of 1.5 g of sodium nitrite. This solution was added to 100 ml of glacial acetic acid containing 1.5 g of cupric chloride. The mixture was then saturated with sulfur dioxide and stirred at 25° for 1 hour. Ice was added to precipitate the sulfonyl chloride as a bright yellow solid; yield: 6.0 g. The infrared spectrum had —$SO_2Cl$ absorption at 1165 and 1360 cm$^{-1}$.

EXAMPLE 89

5-Methyl-2-cyclopentylmethyl-2,3,8,12b-tetrahydro-1H-3a,8-methanodibenzo[3,4:6,7]cyclohepta[1,2-c]pyrrole A solution of 5.0 g of 5-formyl-2-cyclopentylmethyl-2,3,8,12b-tetrahydro-1H-3a,8-methanodibenzo[3,4:6,7]cyclohepta[1,2-c]pyrrole (Example 69) in 120 ml of acetic acid and 10 ml of perchloric acid was hydrogenated in the presence of 1.5 g of 10% Pd/carbon catalyst at 25°, 50 psi hydrogen pressure, overnight. The mixture was filtered and the solvent was evaporated to leave the product, 5-methyl-2-cyclopentylmethyl-2,3,8,12b-tetrahydro-1H-3a,8-methanodibenzo[3,4:6,7]cyclohepta[1,2-c]pyrrole, as an oil.

Calcd. for $C_{25}H_{29}N$: MW = 343.2298 Found (mass spectrum): 343.2308

The hydrochloride salt was obtained by reaction of the free base with HCl(g) in ether.

Other compounds within the scope of this invention that can be made as described previously include compounds of the general formula

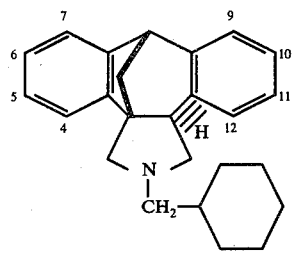

having a single substituent on one of the benzene rings such as the 4-, 5-, 6-, 7-, 9-, 10-, 11- and 12-acetyl derivatives, the 4-, 5-, 6-, 7-, 9-, 10-, 11- and 12-t-butyl derivatives, the 4-, 5-, 6-, 7-, 9-, 10-, 11- and 12-methoxy derivatives, the 4-, 5-, 6-, 7-, 9-, 10-, 11- and 12-fluoro derivatives, the 4-, 5-, 6-, 7-, 9-, 10-, 11- and 12-chloro derivatives, the 4-, 5-, 6-, 7-, 9-, 10-, 11- and 12-difluoromethyl derivatives, the 4-, 5-, 6-, 7-, 9-, 10-, 11- and 12-2,2,2-trifluoroethyl derivatives, the 4-, 5-, 6-, 7-, 9-, 10-, 11-, 12-hydroxyl derivatives, the 4-, 5-, 6-, 7-, 9-, 10-, 11-, 12-bromo derivatives, the 4-, 5-, 6-, 7-, 9-, 10-, 11- and 12-nitro derivatives, the 4-, 5-, 6-, 7-, 9-, 10-, 11- and 12-carboxyl derivatives, the 4-, 5-, 6-, 7-, 9-, 10-, 11- and 12-methoxycarbonyl derivatives, the 4-, 5-, 6-, 7-, 9-, 10-, 11-, and 12-ethoxycarbonyl derivatives, the 4-, 5-, 6-, 7-, 9-, 10-, 11- and 12-amino derivatives, the 4-, 5-, 6-, 7-, 9-, 10-, 11- and 12-formyl derivatives, the 4-, 5-, 6-, 7-, 9-, 10-, 11-, and 12-N-methylsulfamyl derivatives, the 4-, 5-, 6-, 7-, 9-, 10-, 11-, and 12-cyano, the 4-, 5-, 6-, 7-, 9-, 10-, 11-, and 12-acetamido derivatives, the 4-, 5-, 6-, 7-, 9-, 10-, 11-, and 12-formyloxime derivatives, the 4-, 5-, 6-, 7-, 9-, 10-, 11- and 12-acetyloxime derivatives, the 4-, 5-, 6-, 7-, 9-, 10-, 11- and 12-acetyl derivatives, the 4-, 5-, 6-, 7-, 9-, 10-, 11- and 12-propionyl derivatives, the 4-, 5-, 6-, 7-, 9-, 10-, 11- and 12-cyclopentylcarbonyl derivatives, and the 4-, 5-, 6-, 7-, 9-, 10-, 11- and 12-cyclohexylcarbonyl derivatives.

Dosage Forms

The compounds of formula I where R is other than hydrogen show activity in the mammalian central nervous system as clinically useful tranquilizers. These tranquilizing agents can be administered by any means that produces contact of the active agent with the agent's site of action in the body of a mammal. They can be administered by any conventional means available for use in conjunction with pharmaceuticals; either as individual therapeutic agents or in a combination of therapeutic agents. They can be administered alone, but are generally administered with a pharmaceutical carrier selected on the basis of the chosen route of administration and standard pharmaceutical practice.

The dosage administered will, of course, vary depending upon known factors such as the pharmacodynamic characteristics of the particular agent, and its mode and route of administration; age, health, and weight of the recipient; nature and extent of symptoms, kind of concurrent treatment, frequency of treatment, and the effect desired. Usually a daily dosage of active ingredient can be about 0.01 to 200 milligrams per kilogram of body weight. Ordinarily 0.05 to 100, and preferably 0.1 to 50 milligrams per kilogram per day given in divided doses 2 to 4 times a day or in sustained release form is effective to obtain desired results. For the more potent compounds, e.g. trans-2-cyclopentylmethyl-2,3,8,12b-tetrahydro-1H-3a, 8-methanodibenzo[3,4:6,7]cyclohepta[1,2-c]pyrrole (Example 7), the daily dosage ranges are about 0.01 to 100 milligrams per kilogram, preferably 0.05 to 50 milligrams per kilogram, and more preferably 0.1 to 25 milligrams per kilogram.

Dosage forms (compositions) suitable for internal administration contain from about 5 milligrams to about 25 milligrams of active ingredient per unit. In these pharmaceutical compositions the active ingredient will ordinarily be present in an amount of about 0.5 - 95% by weight based on the total weight of the composition.

The active ingredient can be administered orally in solid dosage forms, such as capsules, tablets, and powders, or in liquid dosage forms, such as elixirs, syrups, and suspensions; it can also be administered parenterally, in sterile liquid dosage forms; or rectally in the form of suppositories.

Gelatin capsules contain the active ingredient and powdered carriers, such as lactose, sucrose, mannitol, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration contain preferably a water soluble salt of the active ingredient, suitable stabilizing agents, and if necessary, buffer substances. Antioxidizing agents such as sodium bisulfite, sodium sulfite, or ascorbic acid either alone or combined are suitable stabilizing agents. Also used are citric acid and its salts and sodium EDTA. In addition parenteral solutions can contain preservatives, such as benzalkonium chloride, methyl- or propyl-paraben, and chlorobutanol.

Suppositories contain the active ingredient in a suitable oleaginous or water-soluble base. The oleaginous class includes cocoa butter and fats with similar properties; the water-soluble class includes polyethylene glycols.

Suitable pharmaceutical carriers are described in Remington's Pharmaceutical Sciences, E. W. Martin, a standard reference text in this field.

Useful pharmaceutical dosage-forms for administration of the compounds of this invention can be illustrated as follows:

Capsules

A large number of unit capsules are prepared by filling standard two-piece hard gelatin capsules each with 25 milligrams of powdered active ingredient, 135 milligrams of lactose, 32 milligrams of talc, and 8 milligrams magnesium stearate.

Capsules

A mixture of active ingredient in soybean oil is prepared and injected by means of a positive displacement pump into gelatin to form soft gelatin capsules containing 25 milligrams of the active ingredient. The capsules are washed in petroleum ether and dried.

Tablets

A large number of tablets are prepared by conventional procedures so that the dosage unit is 10 milligrams of active ingredient, 7 milligrams of ethyl cellulose, 0.2 milligram of colloidal silicon dioxide, 7 milligrams of magnesium stearate, 11 milligrams of microcrystalline cellulose, 11 milligrams of cornstarch and 98.8 milligrams of lactose. Appropriate coatings may be applied to increase palatability or delay absorption.

Injectable

A parenteral composition suitable for administration by injection is prepared by stirring 1.5% by weight of active ingredient in 10% by volume propylene glycol and water. The solution is sterilized by filtration.

Suspension

An aqueous suspension is prepared for oral administration so that each 5 milliliters contain 5 milligrams of finely divided active ingredient, 500 milligrams of acacia, 5 milligrams of sodium benzoate, 1.0 gram of sorbitol solution, U.S.P., 5 milligrams of sodium saccharin, and 0.025 milliliter of vanilla tincture.

Injectable

A parenteral composition suitable for administration by injection is prepared by dissolving 1% by weight of active ingredient in sodium chloride injection U.S.P. XV and adjusting the pH of the solution to between 6 and 7. The solution is sterilized by filtration.

Utility

The general tranquilizer activity of the compounds in this series is detected and compared by tests conducted in female white mice in which exploratory loss, ptosis, grip and lift reflexes, catatonia, muscle tone, and pinna twitch reflex are measured; these tests show a good correlation with human efficacy.

Groups of five Carworth $CF_1S$ female mice, 16–20 g each, were fasted 16–22 hours before use. The mice were put in opaque plastic "shoe-box" cages 15–30 min. before injection, and then treated orally with 4, 12, 36, 108 and 324 mg/kg of the compound to be tested as a 13 mg/ml solution in 1% aqueous distilled water solution of methylcellulose (Methocel ®). Each dose was given in a standard volume of 0.45 ml. Observations were made at 0.5, 2 and 24 hours after dosing. $ED_{50}$ values were calculated for each parameter including death $(LD_{50})$. The $ED_{50}$ and $LD_{50}$ values are the doses at which 50% of the naimals would be expected to respond.

Exploratory Activity

The mouse is placed on a stainless steel wire mesh screen (8 × 12 inches, 3 mesh per inch, ¼ inch mesh openings) "shoe-box" lid (1 inch high) and is observed for normal activities, such as nose movements, head movements with apparent visual examination of the area, and/or walking around on the screen. Absence of or marked depression of these activities for 5 seconds constitutes loss of exploratory activity.

Ptosis

The mouse is picked up by the tail and placed on the screen with its head facing the observer. Bilateral eyelid closure of 50% or more two seconds after placement is considered ptosis.

Catatonia

The mouse is placed with its front paws on the edge of a stainless steel "shoe-box" cover, 1 inch high, covered with adhesive tape. Failure to remove both paws from the cover's edge within 5 seconds constitutes catatonia.

Muscle Tone

The observer gently strokes the abdominal musculature of the mouse with thumb and forefinger. Flaccidity (or rarely, tenseness) is recorded.

Grip and Lift Reflexes

The mouse is gently swung by the tail toward a horizontal 12 gauge wire tautly stretched 25 cm above the bench. After the mouse grasps the wire with its forepaws, its posterior end is held directly below the wire. A normal mouse grasps the wire with its forepaws and immediately lifts its hind limbs to the wire. Failure to grasp the wire with the forepaws in both trials constitutes loss of the grip reflex; failure to lift the hind limbs to grasp the wire with at least one hind paw within 5 seconds constitutes loss of the lift reflex.

The ratio of grip to lift response is significant since the loss of lift reflex is much more pronounced in most compounds exhibiting tranquilizing activity.

Pinna Twitch Reflex

The mouse is placed on the bar 10–20 cm horizontally and 9 cm vertically from a Galton whistle adjusted for 13 kc (5 mm on the whistle scale) and is subjected to several short bursts of sound. If the mouse does not twitch its ears or flatten them against its head the pinna reflex is lost.

An effective tranquilizer should induce little or no tremor response. Most of the compounds, as shown in Table I, induce little tremor response in the tested mice. Tremors include fine or coarse and intermittent or continuous tremors.

Mouse Spontaneous Motor Activity (Activity Cage)

Twenty-four per dose, 16–20 g or 18–22 g, female $CF_1S$ mice, fasted 16–22 hours, are intubated (in pairs) with drug at t doses such as 0, 1, 3, 9, 27 and 81 mg/kg in 10 ml/kg of aqueous 1% methylcellulose. The mice are then put in separate "shoe-box" cages (12 × 7.5 × 5.3 inches plastic with a 0.33 inch mesh stainless steel lid), and 20 minutes after intubation the animals in pairs are moved to covered Woodard Photoelectric Activity Chambers (central light source type measurement floor area = 96 in$^2$). Ten minutes later (30 minutes after dosing) a 5-minute count is taken. Counting chamber characteristics are balanced out by counting 2 pairs of mice from each dose level in each of 6 different counting chambers. Half of each test is run in the a.m. and the other half is run in the p.m. to minimize "biological clock" variations.

Since activity counts do not distribute normally and their square roots do, Irwin, S.: Rev. Canad. Biol. 20, 239–50 (1961), raw counts are thus transformed for statistical treatment (Student's t test). The means of the square roots then are squared and an $ED_{50}$ for stimulation or depression (or both) is determined graphically.

With the above-listed responses as criteria, the compounds of the invention exhibit potent tranquilizing activity as shown in Table I. The $ED_{50}$ values, i.e., the dose which caused the response in 50% of the mice, are tabulated. The results obtained in the tests for two well known commercial tranquilizers, Chlorpromazine and Diazepam, are included for comparison.

Several compounds of the invention, especially those of Examples 7 and 25, exhibit potent anti-anxiety or minor tranquilizer activity in addition to their major tranquilizer activity. Potential as anti-anxiety agents was assessed by means of the potency of these compounds in the rat approach-avoidance test. Anti-anxiety agents such as Diazepam are active in this test, but major tranquilizers such as Chlorpromazine are not active at non-sedating doses.

Approach-Avoidance Test Method 18 hr. waterdeprived Holzman male white rats, 150–175 g each, were used. The apparatus consists of two interconnected chambers, the first in which the animal is placed, and a second which contains the stimulus and a water bottle. The second is fitted with an electrifiable floor. On the first day, the rats are placed in the first chamber. They are allowed three minutes to find the water bottle in the second chamber and to drink water for at least two seconds. After three successful trials on the first day the animals are given one predrug trial on the second day. Then follows a second predrug trial during which the floor of the second chamber is electrified 1.5 seconds after the rat has commenced drinking water. The animals are randomized, dosed orally, and reexposed to the test situation at 1, 2, or 4 hours after the shock trial. Solvent-treated rats usually do not reenter the second chamber after the shock trial.

The results of this test are summarized in Table II. The $ED_{50}$ values, i.e., the dose which caused the response in 50% of the rats are tabulated. The results obtained in the test of a well known commercial tranquilizer, Diazepam, are included for comparison.

In addition to their tranquilizer action compounds of formula I where R is other than hydrogen, show activity in the mammalian central nervous system as useful analgesics. The analgesic activity of these compounds was evidenced by tests conducted in female white mice in which prevention of the well-known writhing response caused by intraperitoneal injection of phenyl-p-benzoquinone (phenylquinone) was demonstrated. This mouse test is predictive of analgesic response in humans. [E. Siegmund, R. Cadmus and G. Lee, Proc. Soc. Exp. Biol. Med., 95, 729 (1957)].

Groups of five Carworth $CF_1S$ female mice, 18–21 g each, were fasted 17–21 hours and were intubated with analgesic compound as antagonist to phenylquinone at oral doses of 8, 40 and 200 or of 0.33, 1, 3, 9, 27 and 81 mg/kg in 0.30 ml 1% methylcellulose (Methocel). 30 minutes later the mice were challenged with phenylquinone, 1.1 mg/kg intraperitoneally (dissolved in pure ethanol and diluted to 5% ethanol with distilled water at 40° C). At 37 minutes to 47 minutes after the analgesic compound, the mice were observed for appearance of the writhing syndrome. The number of mice which did not writhe at all during the 10 minutes observation was recorded as a quantal index of analgesia. $ED_{50}$ values were obtained graphically from the data.

With blockade of phenylquinone-induced writhing as the criterion, many of the compounds of the invention are analgesic. The $ED_{50}$ values, i.e., the doses which blocked phenylquinone-induced writhing in 50% of the mice, are also tabulated in Table I.

TABLE 1

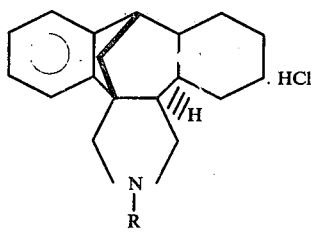

| Active Tranquilizer R | Ex | $Ld_{50}^{(a)}$ (mg/kg) | Phenylquinone Analgesia $ED_{50}$ (mg/kg) | Exploratory Loss Visual | Activity Cage | Ptosis | Catatonia | Muscle Tone | Reflexes Lift | Grip | Pinna | Tremors | $N^{(b)}$ |
|---|---|---|---|---|---|---|---|---|---|---|---|---|---|
| $CH_3$ | 1 | 150 | 5.1 | 50 | — | 50 | 30 | 100 | 30 | 150 | 30 | 30 | 5 |
| Cyclopropylmethyl | 6 | 300 | 4.5 | 20 | — | 20 | 20 | 12 | 20 | 100 | 7 | 100 | 5 |
| Cyclobutylmethyl | 19 | >324 | 5.0 | 20 | 1.0 | 7 | 20 | 12 | 20 | 200 | 12 | >324 | 5 |
| Cyclopentylmethyl | 7 | >324 | 2.0 | 7 | 0.66 | $3^{(c)}$ | 8 | 7 | 11 | 210 | 9 | >324 | 10 |
| Cyclohexylmethyl | 25 | 320 | 6.4 | 9 | 4.7 | $3^{(c)}$ | 9 | 8 | 8 | $450^{(c)}$ | 7 | $450^{(c)}$ | 10 |
| Cycloheptylmethyl | 32 | >324 | 2.9 | 7 | — | <4 | 12 | 36 | 20 | 200 | 60 | >324 | 5 |
| Benzyl | 4 | >324 | 9.4 | 20 | 4.6 | 20 | 20 | 20 | 36 | >324 | 300 | >324 | 5 |
| β-phenylethyl | 39 | >324 | 22.0 | 200 | — | 200 | 100 | >324 | 100 | >324 | 100 | 300 | 5 |
| Allyl | 10 | >324 | 1.9 | 4.5 | — | <3 | 5 | 3.2 | 6 | 150 | 4 | 187 | 10 |
| $CH_2CH_2CH_2CO_2C_2H_5$ | 11 | >324 | 26 | 100 | — | 100 | 100 | 200 | >324 | >324 | 100 | >324 | 5 |
| Ethyl | 12 | 200 | 4.3 | 20 | — | 12 | 12 | 36 | 12 | 100 | 12 | 200 | 5 |
| n-Butyl | 13 | >324 | 10.5 | 12 | — | 7 | 12 | 12 | 7 | 200 | ≦4 | 300 | 5 |
| n-Hexyl | 14 | >324 | 2.6 | 7 | 1.3 | 4.5 | 5.6 | 4.1 | 8.6 | 187 | 11 | $326^{(c)}$ | 10 |
| n-Heptyl | 15 | >324 | 3.6 | $3.2^{(c)}$ | 1.0 | <3 | 5 | $3^{(c)}$ | 9 | 260 | $3.6^{(c)}$ | >324 | 5 |
| n-Octyl | 16 | >324 | 12 | 20 | — | 12 | 12 | 12 | 20 | >324 | 20 | >324 | 5 |
| 2-Ethylbutyl | 17 | >324 | 48 | 200 | — | 100 | 36 | 100 | 200 | >324 | 200 | >324 | 5 |
| Propargyl | 18 | >324 | >135 | 200 | — | 200 | 100 | 300 | 200 | >324 | >324 | >324 | 5 |
| 3-Methylenecyclobutylmethyl | 20 | >324 | 8.2 | 21 | — | 11 | 13 | 15 | 21 | 362 | 24 | >324 | 10 |
| 1-Cyclopentenylmethyl | 21 | >324 | 2.9 | 7 | — | 7 | 20 | 36 | 36 | 300 | 20 | >324 | 5 |
| 2-Cyclopentylethyl | 22 | >324 | 10 | 32 | — | $3^{(c)}$ | 18 | 3.6 | 17 | 265 | 11 | >324 | 10 |
| 2-Cyclopent-2-enylethyl | 23 | >324 | 15 | 57 | — | 46 | 37 | 37 | 88 | 265 | 62 | >324 | 10 |
| 3-Cyclopentylpropyl | 24 | >324 | 6 | 7 | — | 6 | 7 | 6 | 17 | >324 | 17 | >324 | 10 |
| 1-Cyclohexenylmethyl | 26 | >324 | 6.8 | 12 | 0.8 | 6 | 10 | 7 | 15 | 400 | 15 | >324 | 10 |
| 3-Cyclohexenylmethyl | 27 | >324 | 4.2 | 4.5 | 0.29 | 2.9 | 4.5 | 4.5 | 9 | 97 | 8 | >324 | 10 |
| 1,4-Cyclohexadienylmethyl | 28 | >324 | 8.6 | 29 | — | 17 | 24 | 37 | 57 | >324 | 32 | >324 | 10 |
| 2-Cyclohexylethyl | 29 | >324 | 28 | 24 | — | 17 | 21 | 24 | 78 | 290 | 50 | >324 | 10 |
| 3-Cyclohexylpropyl | 30 | >324 | 7 | 4 | — | 4 | 12 | 7 | 12 | 200 | 7 | >324 | 5 |
| 4-Cyclohexylbutyl | 31 | >324 | 14 | 21 | — | 17 | 26 | 24 | 37 | >324 | 32 | >324 | 10 |
| 4-Cycloheptenylmethyl | 33 | >324 | 3.3 | 9 | — | 4 | 11 | 7 | 19 | >324 | 37 | >324 | 10 |
| Cyclooctylmethyl | 34 | >324 | 6 | 40 | — | 4 | 23 | 21 | 62 | >324 | 97 | >324 | 10 |
| 2-Exobicyclo[2.2.1]heptylmethyl | 35 | >324 | 6.2 | 8.6 | 3.3 | 5.1 | 15 | 12 | 29 | >324 | 21 | >324 | 10 |
| 2-Endobicyclo[2.2.1]heptylmethyl | 36 | >324 | 9.8 | 60 | — | 20 | 60 | 60 | 60 | >324 | 100 | >324 | 5 |
| 2-Exobicyclo[2.2.1]hept-5-enylmethyl | 37 | 300 | 2.4 | 7 | — | ≦4 | 7 | 4 | 12 | 200 | 20 | >324 | 5 |
| 2-Endobicyclo[2.2.1]hept-5-enylmethyl | 38 | >324 | 31 | 200 | — | 60 | 100 | 200 | 200 | >324 | >324 | >324 | 5 |
| 2-Phenoxyethyl | 40 | >324 | 5.3 | 60 | — | 7 | 12 | 20 | 20 | >324 | 12 | >324 | 5 |
| 2-Methoxyethyl | 41 | 300 | 4.2 | 20 | — | 20 | 20 | 36 | 36 | 200 | 20 | >324 | 5 |
| 2-Furylmethyl | 42 | 300 | 26 | 60 | — | 20 | 36 | 20 | 200 | >324 | 60 | >324 | 5 |
| 2-Methyl$^{(e)}$ | 43 | 200 | — | 7 | — | 20 | 100 | 20 | 20 | 60 | 20 | 36 | 5 |
| 2-Cyclohexylmethyl$^{(e)}$ | 44 | >324 | — | 17 | — | <3 | 19 | 12 | 36 | >324 | 11 | >324 | 10 |
| Cyclopentylmethyl-N-oxide | 7 | >324 | 24 | 12 | — | ≦4 | 36 | 12 | 20 | >324 | 7 | >324 | 5 |
| Methyl-N-oxide | | >324 | — | 60 | — | 36 | 60 | 100 | 36 | 200 | 60 | 36 | |
| Cyclopropyl | 46 | >324 | 90 | 200 | — | 60 | 200 | 200 | 200 | 300 | 300 | >324 | 5 |
| Cyclobutyl | 47 | >324 | 9.6 | 60 | — | 36 | 60 | 60 | 60 | 200 | 36 | >324 | 5 |
| Cyclopentyl | 48 | >324 | 38. | 100 | — | 60 | 36 | 100 | 60 | 200 | 60 | >324 | 5 |
| Isopropyl | 49 | 200 | 10.8 | 60 | — | 12 | 60 | 7 | 36 | 200 | 20 | >324 | 5 |
| 1-Cyclopentylethyl | 50 | >324 | 23 | 20 | — | 60 | 20 | 36 | 60 | 300 | 36 | >324 | 5 |
| trans-2-Phenylcyclopropylmethyl | 55 | >324 | 48 | 100 | — | 36 | 200 | 100 | 200 | >324 | 200 | >324 | 5 |
| 2-Adamantylmethyl | 53 | >324 | 94 | 60 | — | 300 | 36 | 100 | 300 | >324 | 100 | >324 | 5 |
| t-Butyl | 56 | 300 | 45 | 200 | — | 100 | 200 | 100 | 60 | 100 | 200 | 200 | 5 |
| 2-Methylcyclopentylmethyl | 51 | >324 | 10 | 100 | — | 36 | 60 | 60 | 60 | 300 | 36 | >324 | 5 |
| 3-Methylcyclopentylmethyl | 52 | >324 | 5 | 12 | — | 7 | 12 | 12 | 12 | 200 | 7 | >324 | 5 |
| 2-Thienylmethyl | 54 | >324 | 27 | 200 | — | 60 | 200 | 200 | >324 | >324 | 200 | >324 | 5 |
| 2-Methyl (f) | 57 | 200 | 5 | 20 | — | 12 | >324 | 60 | >324 | >324 | 12 | 100 | 5 |

TABLE 1-continued

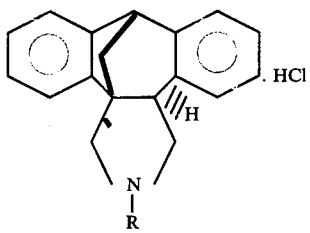

| | | | ED$_{50}$ (mg/kg) | | | | | | | | | |
|---|---|---|---|---|---|---|---|---|---|---|---|---|
| Active Tranquilizer R | Ex | Ld$_{50}$[a] (mg/kg) | Phenylquinone Analgesia ED$_{50}$ (mg/kg) | Exploratory Loss Visual | Activity Cage | Ptosis | Catatonia | Muscle Tone | Reflexes Lift | Grip | Pinna | Tremors | N[b] |
| (−)-Cyclopentylmethyl | 7 | >324 | 1.2 | <4 | — | <4 | 7 | <4 | 4 | 200 | 4 | >324 | 5 |
| (+)-Cyclopentylmetnyl | 7 | >324 | 24. | 36 | — | 20 | 36 | 60 | 60 | 200 | 20 | >324 | 5 |
| n-Propyl | 58 | 200 | 2.9 | 7 | — | 7 | 7 | 7 | 7 | 60 | 4 | — | 5 |
| n-Pentyl | 59 | >324 | 8.2 | 8.4 | — | 4.5 | 17 | 13 | 19 | 100 | 8 | — | 10 |
| 3-Methylbutyl | 60 | >324 | 15 | 20 | — | 36 | 20 | 20 | 60 | 200 | 36 | — | 5 |
| 4-Phenylbutyl | 61 | >324 | 5.6 | 20 | — | 36 | 20 | 20 | 60 | >324 | 36 | — | 5 |
| 2-Tetrahydrofurylmethyl | 62 | >324 | 7 | 12 | — | 7 | 20 | 20 | 20 | 200 | 7 | — | 5 |
| Cyclopentylmethyl (free base) | 7 | >324 | <130 | <3 | — | <3 | 7 | <3 | 4.5 | 260 | <3 | — | 10 |
| Chlopromazine[d] | | 850[c] | — | 7 | 7.3 | 7 | 8 | 8 | 8 | 240 | 5 | >324 | 50 |
| Diazepam | | >1000[c] | — | 87 | 2.0 | 79 | 59 | 89 | 4.4 | 78 | 63 | >324 | 50 |

[a] 24-hour value
[b] Number of mice
[c] Extrapolated value
salt tested free base basis in activity cage test only.

[d] Hydrochloride
[e] Mixture of 5-chloro and 11-chloro substituted compounds.
[f] Mixture of nitro-substituted compounds.

TABLE II

| Active Tranquilizer | Ex. | Dose (mg/kg) | No. of Responders 1 hr | 4 hrs | ED$_{50}$(mg/kg) | N[a] |
|---|---|---|---|---|---|---|
| trans-2-cyclopentylmethyl-2,3,8,12b tetrahydro-1H-3a,8-methanodibenzo[3,4:6,7]cyclohepta[1,2-c]pyrrole | 7 | 0 | — | 2 | | 20 |
| | | 0.03 | — | 1 | | 10 |
| | | 0.1 | — | 7 | | 20 |
| | | 0.3 | — | 6 | 0.2 | 10 |
| trans-2-cyclohexylmethyl-2,3,8,12b tetrahydro-1H-3a,8-methanodibenzo[3,4:6,7]cyclohepta[1,2-c]pyrrole | 25 | 0.1 | — | 1 | | 10 |
| | | 0.3 | — | 2 | | 10 |
| | | 1.0 | — | 5 | 0.5 | 8 |
| Diazepam | — | 0 | 0 | — | | 6 |
| | | 1 | 0 | — | 6 | 6 |
| | | 3 | 2 | — | | 6 |
| | | 10 | 5 | — | 6.0 | 6 |

[a] Number of rats

TABLE III

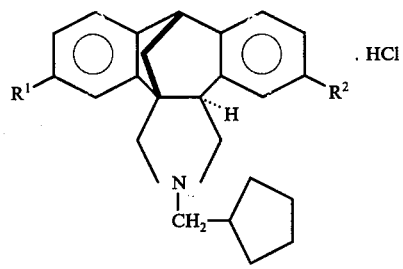

| | | | | ED$_{50}$(mg/kg) | | | | | | | |
|---|---|---|---|---|---|---|---|---|---|---|---|
| Active Tranquilizer R$^1$, R$^2$ | Ex. | LD$_{50}$[a] (mg/kg) | Phenylquinone Analgesia ED$_{50}$ (mg/kg) | Exploratory Loss Visual | Ptosis | Catatonia | Muscle Tone | Reflexes Lift | Grip | Pinna | N[b] |
| R$^1$=NO$_2$; R$^2$=H | 63 | >324 | — | 12 | 7 | 200 | 36 | 100 | >324 | 20 | 5 |
| R$^1$=NH$_2$; R$^2$=H | 64 | >324 | 6.2 | <4 | <4 | <4 | <4 | 12 | 200 | 7 | 5 |
| R$^1$=NHCOCH$_3$; R$^2$=H | 65 | 300 | 18 | 200 | 7 | 60 | 60 | 60 | >324 | 36 | 5 |
| R$^1$=COCH$_3$; R$^2$=H | 66 | >324 | 3.1 | 7 | <4 | 12 | 12 | 20 | 300 | 12 | 5 |
| R$^1$=CH(OH)CH$_3$; R$^2$=H | 67 | >450 | 3.4 | 5 | 3.6 | 5 | 6 | 21 | 187 | 5.6 | 10 |
| R$^1$=OH; R$^2$=H | 68 | >324 | 19 | 12 | 12 | 20 | 20 | 60 | >324 | 36 | 5 |
| R$^1$=CHO; R$^2$=H | 69 | >324 | <130 | 60 | 36 | 60 | 60 | 60 | >324 | 20 | 5 |

TABLE III-continued

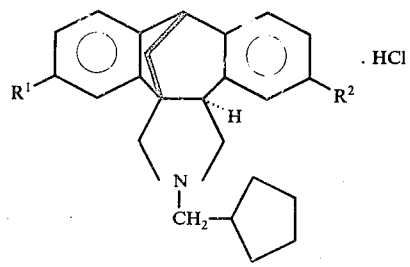

| Active Tranquilizer R¹, R² | Ex. | LD$_{50}$[a] (mg/kg) | Phenyl-quinone Analgesia ED$_{50}$ (mg/kg) | ED$_{50}$(mg/kg) Exploratory Loss Visual | Ptosis | Catatonia | Muscle Tone | Reflexes Lift | Reflexes Grip | Pinna | N[b] |
|---|---|---|---|---|---|---|---|---|---|---|---|
| R¹=Br; R²=H | 70 | >324 | <130 | 20 | 7 | 12 | 12 | 20 | >324 | 7 | 5 |
| R¹=C(CH₃)=NOH; R²=H | 71 | >324 | 21 | 7 | <4 | 100 | 36 | 60 | 300 | 20 | 5 |
| R¹=NH₂; R²=NH₂ | 72 | >324 | 7 | 60 | 7 | 20 | 36 | 60 | 200 | 20 | 5 |
| R¹=CO₂H; R²=H | 73 | >324 | 21 | 60 | 36 | 60 | 36 | 100 | >324 | 36 | 5 |
| R¹=CO₂CH₃; R²=H | 74 | >324 | 11 | 36 | <4 | 36 | 36 | 36 | >324 | 7 | 5 |
| R¹=CH(OH)CH₂CH=CH₂; R²=H | 75 | >324 | 11 | 60 | 12 | 36 | 36 | 20 | 200 | 7 | 5 |
| R¹=Cl; R²=H | 76 | 300 | <130 | 7 | 7 | 12 | 12 | 20 | >324 | 20 | 5 |
| R¹=F; R²=H | 77 | >324 | <130 | 7 | 7 | 20 | 20 | 20 | >324 | 36 | 5 |
| R¹=CHF₂; R²=H | 78 | >324 | <130 | 7 | <4 | 20 | 7 | 20 | >324 | 7 | 5 |
| R¹=Cl; R²=Cl[c] | 79 | >324 | active | 7 | 7 | 20 | 36 | 36 | >324 | 7 | 5 |
| R¹=H; R²=Cl[c] | 80 | 200 | — | 7 | 20 | 100 | 20 | 20 | 60 | 20 | 5 |
| R¹=H; R²=Cl[d] | 81 | >324 | — | 17 | <3 | 19 | 12 | 36 | >324 | 11 | 10 |
| R¹=N₃; R²=H | 82 | >324 | <130 | 7 | 7 | 60 | 20 | 60 | >324 | 36 | 5 |
| R¹=CH=NOH; R²=H | 83 | >324 | 2.7 | 20 | 36 | 36 | 36 | 60 | >324 | 20 | 5 |
| R¹=CH=NOC(=O)NHCH₃ R²=H | 84 | >324 | <130 | 60 | 36 | 100 | 100 | 200 | >324 | 100 | 5 |
| R¹=CN; R²=H | 85 | 300[e] | 1.7 | 4.4 | 4.4 | 15 | 15 | 17 | >324[e] | 9.7 | 10 |
| R¹=CH₂OH; R²=H | 86 | >324 | 26 | 12 | 7 | 60 | 60 | 36 | 200 | 20 | 5 |
| R¹=CH₂F; R²=H | 87 | >324 | 78 | 12 | 7 | 36 | 36 | 36 | 300 | 36 | 5 |
| R¹=SO₂NHCH₃; R²=H | 88 | >324 | <130 | 20 | 36 | 300 | 200 | 200 | >324 | 100 | 5 |
| R¹=CH₃; R²=H | 89 | >81 | — | 9 | 15 | 50 | 50 | 25 | <81 | 15 | 5 |

[a]24-hr value
[b]Number of mice
[c]Substitutent on 2-nitrogen is methyl rather than cyclopentylmethyl
[d]Substitutent on 2-nitrogen is cyclohexylmethyl rather than cyclopentylmethyl
[e]N=5

I claim:
1. A compound of the formula:

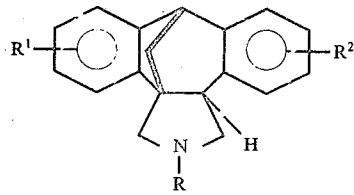

where
R¹ and R², the same or different = hydrogen, lower alkyl, lower alkoxy, hydroxyl, fluorine, chlorine, bromine, 2,2,2-trifluroethyl, carboxyl, methoxycarbonyl, ethoxycarbonyl, N-methylsulfamyl, lower alkylcarbonyl, cycloalkylcarbonyl of 4-7-carbons, nitro, amino, acetamido, formyl, cyano, azido, fluoromethyl, difluoromethyl, formyloxime, acetyloxime,

where R⁶ is hydrogen, lower alkyl, or alkenyl of 3-4 carbons; provided, that only one of R¹ and R² is nitro;
R = hydrogen, alkyl of 1-10 carbons, alkenyl of 3-7 carbons attached by a saturated carbon to N, cycloalkyl of 3-5 carbons, propargyl, α-furylmethyl, α-tetrahydrofurylmethyl, α-thienylmethyl; and —(CH₂)$_n$CN, —(CH₂)$_n$COOH, —(CH₂)$_q$OR³, —(CH₂)$_n$COO (lower alkyl), and —(CH(R⁴)(CH₂)$_p$R⁵ of up to 14 carbons, where
n = 1-6;
p = 0-5;
q = 2-6;
R³ = lower alkyl, phenyl, or lower alkylphenyl;
R⁴ = hydrogen or n-lower alkyl;
R⁵ = a hydrocarbyl group containing at least one ring of 3-9 carbons attached to alkylene by a ring carbon; provided, when p = 0, the carbon attached to —CH(R⁴)— is not a quaternary carbon; and tertiary amine oxides when R is other than hydrogen.
2. The compound of claim 1 where R is hydrogen.
3. A compound of the formula:

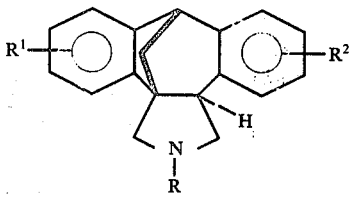

where
R¹ and R², the same or difffferent = hydrogen, lower alkyl, lower alkoxy, hydroxyl, fluorine, chlorine, bromine, 2,2,2-trifluroethyl, carboxyl, methoxycarbonyl, ethoxycarbonyl, N-methylsulfamyl, lower alkylcarbonyl, cycloalkylcarbonyl of 4–7 carbons, nitro, amino, acetamido, formyl, cyano, azido, fluoromethyl, difluoromethyl, formyloxime, acetyloxime,

where $R^6$ is hydrogen, lower alkyl, or alkenyl of 3–4 carbons; provided, that only one of $R^1$ and $R^2$ is nitro;

R = alkyl of 1–10 carbons, alkenyl of 3–7 carbons attached by a saturated carbon to N, cycloalkyl of 3–5 carbons, propargyl, α-furylmethyl, α-tetrahydrofurylmethyl, α-thienylmethyl; and —$(CH_2)_nCN$, —$(CH_2)_nCOOH$, —$(CH_2)_qOR^3$, —$(CH_2)_nCOO$ (lower alkyl), and —$CH(R^4)(CH_2)_pR^5$ of up to 14 carbons, where n = 1–6;
p = 0–5;
q = 2–6;
$R^3$ = lower alkyl, phenyl, or lower alkylphenyl;
$R^4$ = hydrogen or n-lower alkyl;
$R^5$ = a hydrocarbyl group containing at least one ring of 3–9 carbons attached to alkylene by a ring carbon; provided, when p = O, the carbon attached to —$CH(R^4)$— is not a quaternary carbon; and its pharmaceutically suitable salts.

4. The compound of claim 3 where $R^1$ and $R^2$ are each hydrogen.

5. The compound of claim 4 where: R is alkyl of 1–10 carbons, alkenyl of 3–7 carbons joined to N through a saturated carbon atom, α-furylmethyl, —$(CH_2)_q$—O (lower alkyl), —$(CH_2)_q$—O—phenyl, or —$CH(R^4)(CH_2)_pR^5$;

q is 2–6;
p is 0–3;
$R^4$ is H or $CH_3$;
$R^5$ is cycloalkyl of 3 to 8 carbon atoms; cycloalkenyl of 3 to 8 carbon atoms; methylenecycloalkyl of 4 to 9 carbon atoms; polycycloalkyl of 7 to 9 carbon atoms; polycycloalkenyl of 7 to 9 carbon atoms; or phenyl.

6. The compound of claim 5 where R = n-alkyl of 2–8 carbon atoms.

7. The compound of claim 6 where R is n-propyl.

8. The compound of claim 6 where R is n-hexyl.

9. The compound of claim 6 wherein R is n-heptyl.

10. The compound of claim 6 where R is n-pentyl.

11. The compound of claim 5 where R is alkenyl of 3–7 carbons, attached to N by a saturated carbon atom.

12. The compound of claim 11 where R is allyl.

13. The compound of claim 5 where R is —$CH(R^4)(CH_2)_pR^5$, p is 0–3, $R^4$ is H or methyl; and $R^5$ is cycloalkyl of 3–8 carbons; cycloalkenyl of 3–8 carbons; methylenecycloalkyl of 4–9 carbons; polycycloalkyl of 7–9 carbons; polycycloalkenyl of 7–9 carbons; or phenyl.

14. The compound of claim 13 where R is cycloalkylmethyl.

15. The compound of claim 14 where R is cyclopentylmethyl.

16. The levorotatory (−) isomer of the compound of claim 15.

17. The dextrorotatory (+) isomer of the compound of claim 15.

18. The compound of claim 14 where R is cyclohexylmethyl.

19. The compound of claim 14 where R is cycloheptylmethyl.

20. The compound of claim 13 where R is benzyl.

21. The compound of claim 13 where R is cycloalkenylmethyl of 5–8 carbon atoms.

22. The compound of claim 21 where R is 1-cyclopentenylmethyl.

23. The compound of claim 21 where R is 3-cyclohexenylmethyl.

24. The compound of claim 13 where R is 2-exo-bicyclo[2.2.1]heptylmethyl.

25. The compound of claim 13 where R is 2-exo-bicyclo[2.2.1]hept-5-enylmethyl.

26. The compound of claim 13 where R is cyclopentylpropyl.

27. A pharmaceutical composition comprising a suitable pharmaceuutical carrier and an effective tranquilizing amount of a compound of claim 3.

28. A pharmaceutical composition comprising a suitable pharmaceutical carrier and an effective tranquilizing amount of a compound of claim 4.

29. A pharmaceutical composition comprising a suitable pharmaceutical carrier and an effective tranquilizing amount of a compound a claim 5.

30. A pharmaceutical composition comprising a suitable pharmaceutical carrier and an effective tranquilizing amount of a compound of claim 15.

31. A pharmaceutical composition comprising a suitable pharmaceutical carrier and an effective tranquilizing amount of a compound of claim 16.

32. A pharmaceutical composition comprising a suitable pharmaceutical carrier and an effective tranquilizing amount of a compound of claim 17.

33. A pharmaceutical composition comprising a suitable pharmaceutical carrier and and effective tranquilizing amount of a compound of claim 18.

34. A method of tranquilizing a mammal which comprises administering an effective tranquilizing dose of a compound of claim 3.

35. A method of tranquilizing a mammal which comprises administering an effective tranquilizing dose of a compound of claim 4.

36. A method of tranquilizing a mammal which comprises administering an effective tranquilizing dose of a compound of claim 5.

37. A method of tranquilizing a mammal which comprises administering an effective tranquilizing dose of a compound of claim 15.

38. A method of tranquilizing a mammal which comprises administering an effective tranquilizing dose of a compound of claim 16.

39. A method of tranquilizing a mammal which comprises administering an effective tranquilizing dose of a compound of claim 17.

40. A method of tranquilizing a mammal which comprises administering an effective tranquilizing dose of a compound of claim 18.

41. A method of producing analgesia in a mammal which comprises administering an effective analgesic dose of a compound of claim 3.

42. The compound of claim 3 where $R^1$ is amino and $R^2$ is hydrogen.

43. The compound of claim 3 where $R^1$ is cyano and $R^2$ is hydrogen.

* * * * *